United States Patent
Callewaert et al.

(10) Patent No.: US 12,019,076 B2
(45) Date of Patent: Jun. 25, 2024

(54) MEANS AND METHODS FOR SINGLE MOLECULE PEPTIDE SEQUENCING

(71) Applicants: VIB VZW, Ghent (BE); Universiteit Gent, Ghent (BE)

(72) Inventors: Nico Callewaert, Nevele (BE); Sven Eyckerman, Nazareth (BE); Simon Devos, Sint-Michiels (BE)

(73) Assignees: VIB VZW, Ghent (BE); Universiteit Gent, Ghent (BE)

( * ) Notice: Subject to any disclaimer, the term of this patent is extended or adjusted under 35 U.S.C. 154(b) by 0 days.

(21) Appl. No.: 17/817,908

(22) Filed: Aug. 5, 2022

(65) Prior Publication Data

US 2023/0221329 A1 Jul. 13, 2023

Related U.S. Application Data

(63) Continuation of application No. 16/650,230, filed as application No. PCT/EP2018/076532 on Sep. 28, 2018, now Pat. No. 11,573,238.

(30) Foreign Application Priority Data

Sep. 28, 2017 (GB) ...................................... 1715684

(51) Int. Cl.
*G01N 33/68* (2006.01)
*C12N 9/48* (2006.01)
*C12N 9/64* (2006.01)

(52) U.S. Cl.
CPC ......... *G01N 33/6812* (2013.01); *C12N 9/485* (2013.01); *C12N 9/641* (2013.01);
(Continued)

(58) Field of Classification Search
CPC ........ C12N 9/485; C12N 9/641; G01N 33/68; G01N 33/6812; G01N 33/6818; G01N 33/6824
(Continued)

(56) References Cited

U.S. PATENT DOCUMENTS 5,707,804 A 1/1998 Mathies et al.
5,851,840 A 12/1998 Sluka et al.
(Continued)

FOREIGN PATENT DOCUMENTS

JP 2019-523635 A 8/2019
WO WO 2005/044836 A2 5/2005
(Continued)

OTHER PUBLICATIONS

PCT/EP2018/076532, Jan. 31, 2019, International Search Report and Written Opinion.
(Continued)

*Primary Examiner* — Maureen Wallenhorst
(74) *Attorney, Agent, or Firm* — Wolf, Greenfield & Sacks, P.C.

(57) ABSTRACT

The present invention relates to the field of biochemistry, more particularly to proteomics, more particularly to protein sequencing, even more particularly to single molecule peptide sequencing. The invention discloses methods for single molecule protein sequencing and/or amino acid identification using cleavage inducing agents which are not specific for one particular amino acid, cleave polypeptides step by step from the N-terminus onwards and provide information on the identity of the cleaved amino acids based on the kinetics.

14 Claims, 11 Drawing Sheets

Specification includes a Sequence Listing.

(52) U.S. Cl.
CPC ......... *G01N 33/68* (2013.01); *G01N 33/6818* (2013.01); *G01N 33/6824* (2013.01)

(58) Field of Classification Search
USPC ................ 436/86, 89, 149, 164; 435/7.1, 24
See application file for complete search history.

(56) References Cited

U.S. PATENT DOCUMENTS

| | | | |
|---|---|---|---|
| 6,153,442 A | 11/2000 | Pirio et al. | |
| 6,248,518 B1 | 6/2001 | Parkhurst et al. | |
| 6,255,083 B1 | 7/2001 | Williams | |
| 6,762,048 B2 | 7/2004 | Williams | |
| 6,787,308 B2 | 9/2004 | Balasubramanian et al. | |
| 6,846,638 B2 | 1/2005 | Shipwash | |
| 6,869,764 B2 | 3/2005 | Williams et al. | |
| 6,936,702 B2 | 8/2005 | Williams et al. | |
| 7,052,847 B2 | 5/2006 | Korlach et al. | |
| 7,056,661 B2 | 6/2006 | Korlach et al. | |
| 7,229,799 B2 | 6/2007 | Williams | |
| 7,361,466 B2 | 4/2008 | Korlach et al. | |
| 7,968,702 B2 | 6/2011 | Wegener et al. | |
| 8,034,623 B2 | 10/2011 | Oh et al. | |
| 8,084,734 B2 | 12/2011 | Vertes et al. | |
| 8,153,375 B2 | 4/2012 | Travers et al. | |
| 8,192,961 B2 | 6/2012 | Williams | |
| 8,252,910 B2 | 8/2012 | Korlach et al. | |
| 8,257,954 B2 | 9/2012 | Clark et al. | |
| 8,309,330 B2 | 11/2012 | Travers et al. | |
| 8,354,252 B2 | 1/2013 | Wegener et al. | |
| 8,420,366 B2 | 4/2013 | Clark et al. | |
| 8,455,193 B2 | 6/2013 | Travers et al. | |
| 8,530,154 B2 | 9/2013 | Williams | |
| 8,581,179 B2 | 11/2013 | Franzen | |
| 8,846,881 B2 | 9/2014 | Korlach et al. | |
| 8,906,614 B2 | 12/2014 | Wegener et al. | |
| 8,927,212 B2 | 1/2015 | Kong et al. | |
| 8,980,584 B2 | 3/2015 | Williams | |
| 9,062,091 B2 | 6/2015 | Bjornson et al. | |
| 9,404,146 B2 | 8/2016 | Travers et al. | |
| 9,435,810 B2 | 9/2016 | Havranek et al. | |
| 9,464,107 B2 | 10/2016 | Wegener et al. | |
| 9,542,527 B2 | 1/2017 | Travers et al. | |
| 9,551,031 B2 | 1/2017 | Korlach et al. | |
| 9,551,660 B2 | 1/2017 | Kong et al. | |
| 9,566,335 B1 | 2/2017 | Emili et al. | |
| 9,582,640 B2 | 2/2017 | Travers et al. | |
| 9,600,626 B2 | 3/2017 | Travers et al. | |
| 9,625,469 B2 | 4/2017 | Marcotte et al. | |
| 9,678,080 B2 | 6/2017 | Bjornson et al. | |
| 9,719,073 B2 | 8/2017 | Emig et al. | |
| 9,845,501 B2 | 12/2017 | Williams | |
| 9,879,319 B2 | 1/2018 | Korlach et al. | |
| 9,910,956 B2 | 3/2018 | Travers et al. | |
| 9,957,291 B2 | 5/2018 | Sebo et al. | |
| 10,023,605 B2 | 7/2018 | Bjornson et al. | |
| 10,066,258 B2 | 9/2018 | Kong et al. | |
| 10,150,872 B2 | 12/2018 | Zheng et al. | |
| 10,161,002 B2 | 12/2018 | Korlach et al. | |
| 10,481,162 B2 | 11/2019 | Emili et al. | |
| 10,544,449 B2 | 1/2020 | Shen et al. | |
| 10,545,153 B2 | 1/2020 | Marcotte et al. | |
| 10,570,445 B2 | 2/2020 | Kong et al. | |
| 10,676,788 B2 | 6/2020 | Shen et al. | |
| 10,745,750 B2 | 8/2020 | Korlach et al. | |
| 10,787,573 B2 | 9/2020 | Zheng et al. | |
| 11,162,952 B2 | 11/2021 | Marcotte et al. | |
| 11,268,963 B2 | 3/2022 | Emili | |
| 11,573,238 B2 | 2/2023 | Callewaert et al. | |
| 2005/0042633 A1 | 2/2005 | Williams | |
| 2005/0266456 A1 | 12/2005 | Williams et al. | |
| 2007/0072196 A1 | 3/2007 | Xu et al. | |
| 2007/0219367 A1 | 9/2007 | Shchepinov et al. | |
| 2009/0263802 A1 | 10/2009 | Drmanac | |
| 2010/0009872 A1 | 1/2010 | Eid et al. | |
| 2010/0029494 A1 | 2/2010 | Cherkasov et al. | |
| 2010/0035254 A1 | 2/2010 | Williams | |
| 2011/0003343 A1 | 1/2011 | Nikiforov et al. | |
| 2011/0281776 A1 | 11/2011 | Eshoo et al. | |
| 2012/0322692 A1 | 12/2012 | Pham et al. | |
| 2013/0316912 A1 | 11/2013 | Bjornson et al. | |
| 2014/0273004 A1 | 9/2014 | Havranek et al. | |
| 2015/0087526 A1 | 3/2015 | Hesselberth | |
| 2017/0136433 A1 | 5/2017 | Sun et al. | |
| 2018/0211003 A1 | 7/2018 | Travers et al. | |
| 2018/0299460 A1 | 10/2018 | Emili | |
| 2018/0346507 A1 | 12/2018 | Sebo et al. | |
| 2019/0010183 A1 | 1/2019 | Bjornson et al. | |
| 2019/0249153 A1 | 8/2019 | Kamtekar et al. | |
| 2020/0141944 A1 | 5/2020 | Emili et al. | |
| 2020/0148727 A1 | 5/2020 | Tullman et al. | |
| 2020/0209249 A1 | 7/2020 | Reed et al. | |
| 2020/0209253 A1 | 7/2020 | Reed et al. | |
| 2020/0217853 A1 | 7/2020 | Estandian et al. | |
| 2020/0231956 A1 | 7/2020 | Callewaert et al. | |
| 2020/0400677 A1 | 12/2020 | Boyden et al. | |
| 2021/0148922 A1 | 5/2021 | Dyer et al. | |
| 2021/0396762 A1 | 12/2021 | Chee et al. | |
| 2022/0227889 A1* | 7/2022 | Gunderson | C07K 14/195 |
| 2022/0291226 A1* | 9/2022 | Boyden | G01N 21/76 |
| 2023/0016396 A1* | 1/2023 | Gunderson | G01N 33/582 |
| 2023/0032607 A1* | 2/2023 | Feng | G01N 33/6803 |
| 2023/0076975 A1* | 3/2023 | Anslyn | C12N 9/50 |
| 2023/0104998 A1* | 4/2023 | Estandian | G01N 33/58 |
| | | | 436/89 |
| 2023/0213527 A1* | 7/2023 | Reed | G01N 33/6893 |
| | | | 436/85 |

FOREIGN PATENT DOCUMENTS

| | | | |
|---|---|---|---|
| WO | WO 2007/070572 A2 | 6/2007 | |
| WO | WO 2010/065322 A1 | 6/2010 | |
| WO | WO 2010/115016 A2 | 10/2010 | |
| WO | WO 2017/063093 A1 | 4/2017 | |
| WO | WO 2019/040825 A1 | 2/2019 | |

OTHER PUBLICATIONS

PCT/EP2018/076532, Apr. 9, 2020, International Preliminary Report on Patentability.

International Search Report and Written Opinion for Application No. PCT/EP2018/076532 dated Jan. 31, 2019.

International Preliminary Report on Patentability for Application No. PCT/EP2018/076532, dated Apr. 9, 2020.

Koushik et al., Cerulean, Venus, and VenusY67C FRET reference standards. Biophys J. Dec. 15, 2006;91(12):L99-L101. doi: 10.1529/biophysj.106.096206. Epub Oct. 13, 2006. PMID: 17040988; PMCID: PMC1779932.

Saito et al., Dual-labeled oligonucleotide probe for sensing adenosine via FRET: a novel alternative to SNPs genotyping. Chem Commun (Camb). Jun. 7, 2007;(21):2133-5. doi: 10.1039/b618465k. Epub Feb. 2, 20078. PMID: 17520113.

Sato et al., Polyproline-rod approach to isolating protein targets of bioactive small molecules: isolation of a new target of indomethacin. J Am Chem Soc. Jan. 31, 2007;129(4):873-80. doi: 10.1021/ja0655643. PMID: 17243824.

Stryer et al., Energy transfer: a spectroscopic ruler. Proc Natl Acad Sci U S A. Aug. 1967;58(2):719-26. doi: 10.1073/pnas.58.2.719. PMID: 5233469; PMCID: PMC335693.

Williams et al., An artificial processivity clamp made with streptavidin facilitates oriented attachment of polymerase-DNA complexes to surfaces. Nucleic Acids Res. Oct. 2008;36(18):e121. doi: 10.1093/nar/gkn531. Epub Aug. 22, 2008. PMID: 18723573; PMCID: PMC2566871.

[No Author Listed], aminopeptidase [Thermus aquaticus]. NCBI Reference Sequence: WP_053768123.1. GenBank. Jun. 8, 2016. https://www.ncbi.nlm.nih.gov/protein/927055022?sat=51&satkey=55916985 (Last accessed Jun. 19, 2023). 1 page.

\* cited by examiner

MEANS AND METHODS FOR SINGLE MOLECULE PEPTIDE SEQUENCING

RELATED APPLICATIONS

This application is a continuation application of U.S. application Ser. No. 16/650,230, filed Mar. 24, 2020, now U.S. Pat. No. 11,573,238, which is a U.S. national phase application of PCT International Patent Application No. PCT/EP2018/076532, filed Sep. 28, 2018, which claims priority to United Kingdom Application No. 1715684.5, filed Sep. 28, 2017, each of which is hereby incorporated by reference in its entirety.

REFERENCE TO AN ELECTRONIC SEQUENCE LISTING

The contents of the electronic sequence listing (R070870106US01-SEQ-MKN.xml; Size: 14,855 bytes; and Date of Creation: Aug. 5, 2022) is herein incorporated by reference in its entirety.

FIELD OF THE INVENTION

The present invention relates to the field of biochemistry, more particularly to proteomics, more particularly to protein sequencing, even more particularly to single molecule peptide sequencing. The invention discloses means and methods for single molecule protein sequencing and/or amino acid identification using cleavage-inducing agents. Said cleavage-inducing agents, which are not specific for one particular amino acid, cleave polypeptides step by step from the N-terminus onwards and provide information on the identity of the cleaved amino acids based on the kinetics of the engagement between said cleavage inducing agent with the polypeptide or on the kinetics of said polypeptide cleaving reaction.

BACKGROUND

Technologies for high throughput sequencing of biomolecules (DNA, RNA, protein) are rapidly evolving and are critical for modern science and medicine. In particular, sequencing technologies for DNA has taken giant leaps, now moving from next-generation to third generation approaches acting on single molecule level (e.g. Pacific Biosciences, Oxford Nanopores; Ambardar et al. 2016 Indian J Microbiol 56:394-404). The uniform nature of DNA and the broad panel of available molecular tools has truly pushed the field forward. In contrast, protein/peptide sequencing is lagging behind, and is largely depending on liquid chromatography-mass spectrometry (LC-MS) based technology. Although LC-MS instrumentation has advanced considerably in terms of speed, sensitivity and resolution, operating and maintaining the machinery is highly complex and expensive. Moreover, MS-based proteomics still requires approximately $10^6$ copies of a protein/peptide in order to be detected. Single protein/peptide sequencing is currently not possible, and applications such as single cell proteomics are therefore beyond reach. Moreover, since proteins cannot be amplified in the way that DNA can, single molecule sequencing is conceptually a better match, and would furthermore allow for digital quantification of proteins.

Concepts for next-generation protein sequencing are now germinating, but are facing major challenges. First, there are twenty amino acids to differentiate (as compared to only four nucleotides), and obtaining a single measurable parameter to rigorously identify every amino acid appears unlikely. However, being able to ascribe a certain amino acid category to each sequence position even in a probabilistic manner may already be sufficient for profiling by means of constraint-based peptide identification from databases (as done for LC-MS data) (Swaminathan et al. 2015 PLoS Comput Biol. 11:e1004080). Second, proteins are extremely heterogeneous in terms of physiochemical properties. This can be decreased to some extent by applying the bottom-up proteomics approach, i.e. the protease-mediated digestion of the proteome into peptides. The parallel sequencing of such a complex mixture of peptides, with a dynamic range of several orders of magnitude, will inevitably be facing huge technical hurdles. Complexity can be further decreased by purifying a subset of (proteotypic) peptides from the peptide pool. The sequencing of peptides through (solid-state) nanopores is currently the most popular platform under study. Extensive research is done on the engineering of nanopores that are able to translocate peptides and differentiate between amino acids or amino acid categories along the sequence (Kennedy et al. 2016 Nat Nanotechnol 11:968-976; Wilson et al. 2016 Adv Funct Mater 26:4830-4838).

One other promising technology for the analysis of proteins in a sensitive and quantitative manner was developed by Mitra et al (WO 2010/065531). This technology, referred to as Digital Analysis of Proteins by End Sequencing or DAPES, features a method for single molecule protein analysis. To perform DAPES, a large number of proteins are denatured and cleaved into peptides. These peptides are immobilized on a nanogel surface applied to the surface of a microscope slide and their amino acid sequences are determined in parallel using a method related to Edman degradation. Phenyl isothiocyanate (PITC) is added to the slide and reacts with the N-terminal amino acid of each peptide to form a stable phenylthiourea derivative. Next, the identity of the N-terminal amino acid derivative is determined by performing, for example, 20 rounds of antibody binding with antibodies specific for each PITC-derivatized N-terminal amino acid, detection, and stripping. The N-terminal amino acid is removed by raising the temperature or lowering pH, and the cycle is repeated to sequence 12-20 amino acids from each peptide on the slide. The absolute concentration of every protein in the original sample can then be calculated based on the number of different peptide sequences observed. The PITC chemistry used in DAPES is the same used in Edman degradation and is efficient and robust (>99% efficiency). However, the cleavage of single amino acids requires strong anhydrous acid or alternatively, an aqueous buffer at elevated temperatures. Cycling between either of these harsh conditions is undesirable for multiple rounds of analysis on sensitive substrates used for single molecule protein detection (SMD).

An alternative peptide sequencing method uses N-terminal amino acid binding proteins (NAABs) instead of antibodies that bind PITC-derivatized N-terminal amino acids (WO20140273004). For every amino acid such a NAAB is developed which can be modified from an aminopeptidase or a tRNA synthetase. The NAABs are differently labelled and the N-terminal amino acid of a polypeptide is then identified by detecting the fluorescence label of a specific NAAB that is bound to the N-terminal amino acid upon incubation and washing of such NAABs. Moreover instead of a chemical/physical removal of the N-terminal amino acids, an enzyme called Edmanase (named after the Edman degradation) can be used. Although the Edmanase partially solves limitations from Mitra et al, this method relies on an arsenal of NAABs to derive amino acid identity information.

NAABs for all different amino acids should be present together or added sequentially, adding complexity to this system. Moreover, the ability to develop NAABs with sufficient affinity to be used in single molecule sensing remains undemonstrated. Consequently, it would be advantageous to develop a more simple and elegant protein sequencing technology based on different physiochemical principles than mere binding affinity of reagents.

SUMMARY

Here, an alternative single molecule peptide sequencing method and engineered molecules involved therein are described. The N-terminal amino acid of single molecules of peptides are identified (or categorized) using the catalytic properties of an aminopeptidase and the kinetics of the enzymatic reaction. The method described in this application is based on the correlation between the turnover number ($k_{cat}$) of engineered aminopeptidases and the N-terminal amino acid which it cleaves. Therefore, by measuring the time the engineered aminopeptidase resides upon addition on the peptide substrate before the N-terminal amino acid is cleaved off, N-terminal amino acid is identified. Said aminopeptidase can also be replaced by a chemical cleavage-inducing agent. Similar to what is observed using aminopeptidases, the residence time of chemical cleavage-inducing agents is a read-out for the identity of the N-terminal amino acid to which it binds. More precisely, the application provides a method to sequence proteins comprising the following step cycle: the N-terminal derivatization of peptides immobilized through a moiety of the peptide C-terminal to the scissile bond, measuring the time it takes for a cleavage-inducing agent to cleave off the N-terminal amino acid, leading to release of the N-terminal amino acid from the immobilisation surface, setting the system ready for the next cycle (FIG. 1). The cleavage-inducing agent can be a catalytically active aminopeptidase or isothiocyanate-like chemicals.

In a first aspect, an engineered, catalytically active aminopeptidase acting on a polypeptide is provided, wherein said polypeptide is immobilized on a surface via its C-terminus or via a peptide moiety C-terminal to the first peptide bond of said polypeptide, wherein said aminopeptidase cleaves the N-terminal amino acid of said polypeptide, and wherein the residence time of said aminopeptidase until cleavage of said N-terminal amino acid identifies or categorizes said N-terminal amino acid. Said N-terminal amino acid can be a derivatized N-terminal amino acid and if so said aminopeptidase binds and cleaves said derivatized N-terminal amino acid. Said N-terminal amino acid can be an N-terminal amino acid derivatized with isothiocyanate or isothiocyanate analogues. More particularly said above aminopeptidase is an aminopeptidase having at least 80% sequence identity to SEQ ID No. 1 or to SEQ ID No. 2 and having a glycine residue at position 25, a serine residue at position 65, a cysteine residue at position 138 and a histidine residue at position 208, said aminopeptidase is able to bind N-terminal amino acids derivatized with CITC or SPITC. More particularly said, aminopeptidase comprises an amino acid sequence as depicted in SEQ ID No. 3 or in SEQ ID No. 4.

Said aminopeptidase of current application can also have at least 80% sequence identity to SEQ ID No. 7, wherein a cysteine residue is inserted between the methionine residue at position 1 and the alanine residue at position 2. More particularly said aminopeptidase comprises or consists of SEQ ID No. 8. In particular embodiments, above aminopeptidases further comprise an optical, electrical or plasmonic label, hence said aminopeptidase can be detected optically, electrically or plasmonically. In other particular embodiments, said aminopeptidases are thermophilic and/or solvent resistant.

In a second aspect the use is provided of a cleavage-inducing agent to obtain sequence information of a polypeptide immobilized on a surface via its C-terminus or via a peptide moiety C-terminal to the first peptide bond of said polypeptide, wherein the residence time of said cleavage-inducing agent on the N-terminal amino acid of said polypeptide identifies or categorizes said N-terminal amino acid. Said cleavage-inducing agent can be a catalytically active aminopeptidase, isothiocyanate or an isothiocyanate analogue. More particularly, said catalytically active aminopeptidase can be any of the aminopeptidases described in current application. In particular embodiments, said N-terminal amino acid is selected from the list consisting of Leu, Met, Tyr, Arg, Pro, Gly, Lys, Ala and Val. Above uses are also provided said N-terminal amino acid is a derivatized N-terminal amino acid and for obtaining sequence information at a single molecule level.

In a third aspect, methods are provided of identifying or categorizing the N-terminal amino acid of a polypeptide immobilized on a surface via its C-terminus or via a peptide moiety C-terminal to the first peptide bond of said polypeptide, said method comprising contacting said surface immobilized polypeptide with a cleavage-inducing agent, wherein said cleavage-inducing agent binds and cleaves the N-terminal amino acid from said polypeptide; measuring the residence time of said cleavage-inducing agent on said N-terminal amino acid; and comparing said measured residence time to a set of reference residence time values characteristic for said cleavage-inducing agent and a set of N-terminal amino acids to identify or categorize said N-terminal amino acid.

In the same line, methods are provided of obtaining sequence information of a polypeptide immobilized on a surface via its C-terminus, said method comprising:
 a) contacting said surface-immobilized polypeptide with a cleavage-inducing agent, wherein said agent binds and cleaves the N-terminal amino acid from said polypeptide;
 b) measuring the residence time of said cleavage-inducing agent on the N-terminal amino acid of said surface-immobilized polypeptide;
 c) allowing said cleavage-inducing agent to cleave off said N-terminal amino acid;
 d) identifying or categorizing said N-terminal amino acid by comparing said measured residence time to a set of reference residence time values characteristic for said cleavage-inducing agent and a set of N-terminal amino acids;
 e) repeating steps a) through d) one or more times or repeating steps b) through d) one or more times.

Also provided are above methods, wherein said cleavage-inducing agent is isothiocyanate or isothiocyanate analogues, wherein said residence time is the length of time until said N-terminal amino acid is removed, wherein said N-terminal amino acid is identified by comparing said length of time to a set of reference values for different amino acids.

Also provided are above methods, wherein said cleavage-inducing agent is an aminopeptidase and wherein the residence time of said aminopeptidase is measured for every binding event of said aminopeptidase to said N-terminal amino acid.

The method of the application can additionally include a step of determining the cleavage of said N-terminal amino acid by measuring an optical, electrical or plasmonical signal of the surface-immobilized polypeptide, wherein a difference in optical, electrical or plasmonical signal is indicative for cleavage of said N-terminal amino acid. The above methods are also provided wherein said surface-immobilized polypeptide is additionally contacted with one or more N-terminal amino acid binding proteins, wherein the kinetics of the binding events of said one or more binding proteins to said N-terminal amino acid identify or is further informative for said N-terminal amino acid. The above methods can also include a first step of polypeptide denaturation or are provided in which polypeptide denaturing conditions are present during one or more of the steps of said methods, wherein said catalytically active aminopeptidase is a thermophilic and/or solvent resistant aminopeptidase and/or wherein said cleavage-inducing agent is isothiocyanate or isothiocyanate analogues. Above methods are also provided wherein N-terminal amino acid is derivatized. The aminopeptidase from above methods can be any of the aminopeptidase disclosed herein.

In particular embodiments, the methods of the application are envisage to use a single molecule level. Especially for these application it is foreseen to measure the residence time of the cleavage-inducing agents optically, electrically or plasmonically. This can be done in high throughput when said polypeptide are immobilized on an active sensing surface. Said active sensing surface can be either a gold surface or an amide-, carboxyl-, thiol- or azide-functionalized surface on which said polypeptide is chemically coupled.

DETAILED DESCRIPTION

Definitions

Figure 1:
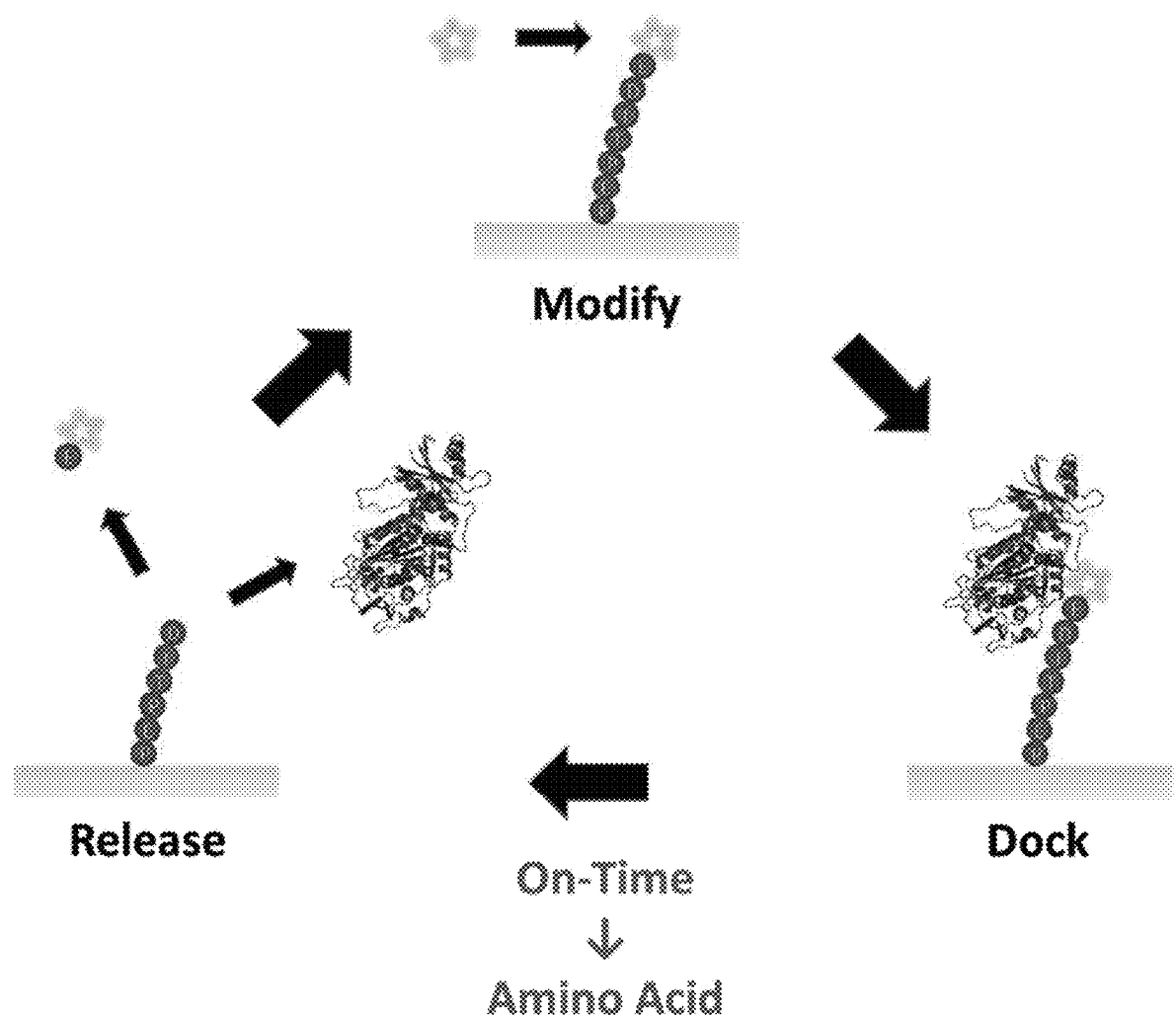
FIG. 1. Kinematic monitoring of enzymatic degradation, more precisely N-terminal amino acid cleavage for single molecule peptide sequencing.

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. The following terms or definitions are provided solely to aid in the understanding of the invention. Unless specifically defined herein, all terms used herein have the same meaning as they would to one skilled in the art of the present invention. Practitioners are particularly directed to Michael R. Green and Joseph Sambrook, Molecular Cloning: A Laboratory Manual, $4^{th}$ ed., Cold Spring Harbor Laboratory Press, Plainsview, New York (2012); and Ausubel et al., Current Protocols in Molecular Biology (Supplement 47), John Wiley & Sons, New York (1999), for definitions and terms of the art. The definitions provided herein should not be construed to have a scope less than understood by a person of ordinary skill in the art.

In current application, Applicants describe a method of peptide sequencing using a multiple step approach in which the N-terminal amino acids are identified one by one. More precisely a method of sequencing a polypeptide is provided, wherein said method comprises the steps of: a) contacting said polypeptide with a cleavage-inducing agent, more particularly a catalytically active aminopeptidase, isothiocyanate or isothiocyanate analogues; b) measuring the residence time of said agent on the N-terminal amino acid of said polypeptide or alternatively measuring the $k_{cat}$ value of said enzymatic reaction; c) identifying or categorizing said N-terminal amino acid by said residence time or said $k_{cat}$ value; and d) repeating the steps a) through c) one or more times. In one embodiment, said polypeptide is immobilized on a surface. It goes without saying that when said agent cleaves the N-terminal amino acid from said polypeptide that said polypeptide is immobilized on a surface by its C-terminus. And vice versa, when said agent cleaves the C-terminal amino acid from said polypeptide that said polypeptide is immobilized on a surface by its N-terminus. In another embodiment, said method is a method of sequencing a surface-immobilized polypeptide at single molecule level.

Given that the described peptide sequencing method relies on the sequential identification of N-terminal amino acids, current application equally discloses a method of identifying or categorizing the N-terminal amino acid of a polypeptide by determining the residence time of a cleavage-inducing agent (more particularly a catalytically active aminopeptidase, isothiocyanate or isothiocyanate analogues) on said N-terminal amino acid, said method comprising contacting said polypeptide with said agent and measuring the residence time of said agent or alternatively the $k_{cat}$ value of said enzymatic reaction. Also in this case, said method can be used on single molecule level with or without the use of surface immobilized peptides. Therefore in one embodiment, said method identifies or categorizes the N-terminal amino acid of a surface-immobilized polypeptide at a single molecule level.

As used herein, the terms "peptide" and "polypeptide" are used interchangeably and refer to a polymeric form of amino acids of any length, which can include coded and non-coded amino acids, natural and non-natural amino acids, chemically or biochemically modified or derivatized amino acids, and polypeptides having modified peptide backbones. As used herein "peptides" or "polypeptides" are shorter than the full-length protein from which they derive and are formed for example but without the purpose of limiting by trypsin or proteinase K protein digestion. In particular embodiments, said peptides or polypeptides have a length between 20 and 500, or between 25 and 200 or between 30 and 100 amino acids or have a length of less than 500, less than 250, less than 200, less than 150, less than 100 or less than 50 amino acids. In any case, "peptide" or "polypeptide" comprises at least 2, at least 3, at least 4, at least 5, at least 6, at least 7, at least 8, at least 9, at least 10 or at least 20 amino acids.

"Single-molecule" as used in single molecule manner or at a single molecule level or in single molecule experiment refers to the investigation of the properties of individual molecules. Single-molecule studies may be contrasted with measurements on an ensemble or bulk collection of molecules, where the individual behavior of molecules cannot be distinguished, and only average characteristics can be measured.

Proteins are amino acid polymers. A protein is created by ribosomes that "read" RNA that is encoded by codons in the gene and assemble the requisite amino acid combination from the genetic instruction, in a process known as translation. The newly created protein strand then undergoes post-translational modification, in which additional atoms or molecules are added, for example copper, zinc, or iron. Once this post-translational modification process has been completed, the protein begins to fold (sometimes spontaneously and sometimes with enzymatic assistance), curling up on itself so that hydrophobic elements of the protein are buried deep inside the structure and hydrophilic elements end up on the outside. The final shape or structure of a protein determines how it interacts with its environment. As such, proteins have a primary structure (i.e. the sequence of amino acids held together by covalent peptide bonds), secondary structure (i.e. regular repeating patterns such as alpha-helices and beta-pleated sheets), tertiary structure (i.e. covalent interactions between amino acid side-chains such as disulfide bridges between cysteine groups) and quaternary structure (i.e. protein sub-units that interact with each other). However, for the methods disclosed in the application, the protein and its N-terminal amino acid should be accessible for the aminopeptidase of the application and preferably the protein is immobilized in a linear configuration. Therefore, in various embodiments, the protein to be sequenced is to be denatured. Denaturation is a process in which proteins lose the quaternary structure, tertiary structure and secondary structure which is present in their native state, but the peptide bonds of the primary structure between the amino acids are left intact. Protein denaturation can be achieved by applying external stresses or compounds such as a strong acid or base, a concentrated inorganic salt, an organic solvent (e.g., alcohol or chloroform), radiation or heat. Therefore, in various embodiments of the application, the aminopeptidases to be used are thermophilic and/or solvent resistant (see later). "Thermophilic" as used herein refers to "increased temperature tolerant", more precisely to an organism or enzyme among others that thrives or maintains its activity at relatively high temperatures between 40 and 122° C. A non-limiting example of a thermophilic organism is *Thermus aquaticus* and accordingly its enzymes such as its aminopeptidase T function at high temperature and are thus thermophilic. In particular embodiments, the aminopeptidases for the uses and methods of current application have optimal peptidase activity in a temperature range of 40° C. and 100° C. or of 40° C. and 80° C. or of 50° C. and 70° or of 60° C. and 80° C. In other particular embodiments, the aminopeptidases of the application maintain their enzymatic activity in the presence of solvents as acetic acid, trichloroacetic acid, sulfosalicylic acid, sodium bicarbonate, ethanol, alcohol, cross-linking agents such as formaldehyde and glutaraldehyde, chaotropic agents such as urea, guanidinium chloride or lithium perchlorate, agents that break disulfide bonds such as 2-mercaptoethanol, dithiothreitol, or tris(2-carboxyethyl)phosphine.

The use of a thermophilic and/or solvent resistant aminopeptidase is especially helpful to fine-tune the "on-time" values of said aminopeptidase upon binding to different N-terminal amino acids. By changing the reaction conditions during the experiment (e.g. protein sequencing) the temperature, the pH, solvents, . . . can be adjusted to differentiate more between the "on-time" value for amino acid X comparted to the "on-time" value for amino acid Y.

In the methods of current application N-terminal amino acids are cleaved from the polypeptide substrate. This can be achieved enzymatically for example chemically or by peptidases, more particularly aminopeptidase. Said cleavage-inducible agents can covalently or non-covalently bind to said N-terminal amino acids.

Chemical Cleavage-Inducing Agents

Figure 15:
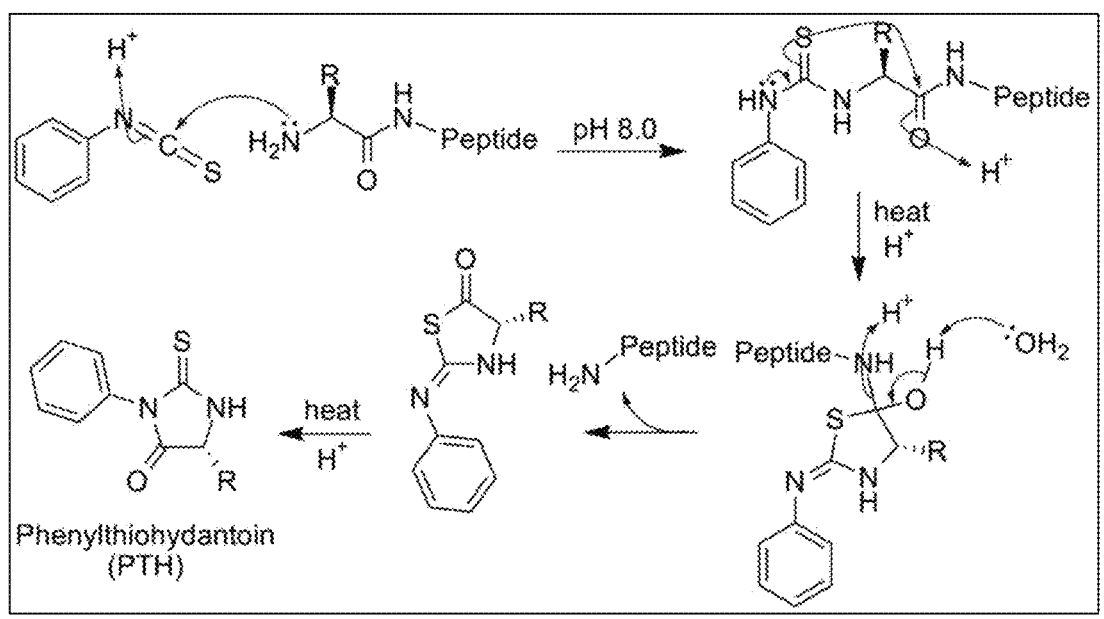
FIG. 15. Schematic representation of the Edman degradation mechanism. Edman degradation entails the coupling of phenyl isothiocyanate (PITC) onto the free N-terminus of a protein/peptide (alkaline conditions), followed by the release of the N-terminal amino acid as a phenylthiohydantoin (PTH) derivative (acidic conditions). The released PTH-amino acid is then identified with chromatography. The procedure is then continually repeated leading to protein/peptide sequence information (source: https://en.wikipedia.org/wiki/Edman_degradation).

Edman degradation is a chemical technique that allows N-terminal sequencing of proteins. It was first described by Pehr Edman in 1950, and in 1967 the degradation reaction was fully automated. The method entails the coupling of phenyl isothiocyanate (PITC) onto the free N-terminus of a protein/peptide (alkaline conditions), followed by the release of the N-terminal amino acid as a phenylthiohydantoin (PTH) derivative (acidic conditions) (FIG. 15). The released PTH-amino acid is then identified with for example chromatography. The procedure is then continually repeated leading to protein/peptide sequence information.

In current application it is surprisingly found that even in the absence of acidic conditions or heat PTH is released and thus the N-terminal amino acid is cleaved from the polypeptide substrate. Even more surprisingly the inventors found that the time between binding isothiocyanate (or analogues) on and the cleavage of the N-terminal amino acid depends on the characteristics of the amino acid. Hence, by measuring said length of time, which is basically the residence time of isothiocyanate (or analogues) on the N-terminal amino acid, the N-terminal amino acid can be identified.

In one preferred embodiment of this application, the cleavage-inducing agent referred to in the uses and methods of the application is a chemical agent, more particularly a chemical agent selected from the list consisting of isothiocyanate (ITC), phenyl isothiocyanate (PITC), azido-PITC, coumarinyl-isothiocyanate (CITC) and sulfophenyl isothiocyanate (SPITC). In current application PITC, azido-PITC, CITC and SPITC will be referred to as isothiocyanate analogues. Hence, the method of current application are provided wherein the cleavage-inducing agent is isothiocyanate or an isothiocyanate analogue.

Also provided herein is the use of a cleavage inducing agent to obtain sequence information of a polypeptide immobilized on a surface via its C-terminus, wherein the residence time of said cleavage-inducing agent on the N-terminal amino acid of said polypeptide identifies said N-terminal amino acid. In particular embodiments, said cleavage-inducing agent is isothiocyanate or an isothiocyanate analogue and said residence time is the length of time between binding of ITC or an ITC analogue on an N-terminal amino acid and removal of said N-terminal amino acid. Said N-terminal amino acid can subsequently be identified by comparing said length of time to a set of reference values obtained for ITC or ITC analogues for different amino acids.

Aminopeptidases

"Aminopeptidase" as used herein refers to an enzyme that catalyzes the cleavage of amino acids from the amino terminus (N-terminus) of protein or peptide substrates. They are widely distributed throughout the animal and plant kingdoms and are found in many subcellular organelles, in cytosol, and as membrane components. Aminopeptidase are classified by 1) the number of amino acids cleaved from the amino terminus of substrates (e.g. aminopeptidases remove intact amino terminal dipeptides, aminotripeptidases catalyze the hydrolysisis of amino terminal tripeptides), 2) the location of the aminopeptidase in the cell, 3) the susceptibility to inhibition by bestatin, 4) the metal ion content and/or residues that bind the metal to the enzyme, 5) the pH at which maximal activity is observed and 6) which is most relevant for this application by the relative efficiency with which residues are removed (Taylor 1993 FASEB J 7:290-298). Aminopeptidases can have a broad or a small substrate specificity. In this application the focus is on the development or use of broad substrate specificity aminopeptidases, however the use of multiple aminopeptidases with substrate specificities that overlap or are complementary are also envisaged in this application.

In general, an enzyme's specificity for a particular substrate under particular environmental conditions can be quantified by the specificity constant $k_{cat}/K_M$. $k_{cat}$ is the turnover number, the number of substrate molecules each enzyme site converts to product per unit of time, or the number of productive substrate to product reaction per catalytic center and per unit of time. $K_M$ is defined as the substrate concentration required for the enzyme to reach half of its maximal velocity under the conditions required for valid steady state enzyme kinetics measurements, well known in the art. When distinguishing two enzyme substrates A and B, based on the rate of conversion of these substrates to products, relations of this type hold:

$$\frac{v_A}{v_B} = \frac{dP_A}{dP_B} = \frac{(V_{Amax}/K_{MA})[A]}{(V_{Bmax}/K_{MB})[B]} = \frac{(k_A/K_{MA})[A]}{(k_B/K_{MB})[B]}$$

with v velocity, and [A] the concentration of A.

Consequently, information on the identity of different substrates of an enzyme can be gained from conversion velocity measurements of these substrates by the enzyme. Under conditions of equal substrate concentrations, relative velocities are determined by $k_{cat}$ and $K_M$. When observing a single substrate molecule, once the enzyme is added, the time required to form a product molecule is governed by $k_{cat}$. Hence, in single molecule observations, information on the identity of the substrate can be gained from the "on-time" or residence time of the enzyme on the substrate. This information can further be complemented by engineering the substrates and/or the enzyme such that catalytically productive engagements of the enzyme and substrate can be distinguished from non-productive ones. Thus "on-time" as used herein refers to the residence time of the enzyme on the substrate, the contact time of the enzyme solution with the substrate or more particularly to the inverse of $k_{cat}$, which is well known in the art. From here on "on-time" and residence time will be used interchangeably and can refer to the time of one enzyme molecule acting on one peptide molecule until cleavage occurs or to the time required for multiple enzyme molecules acting sequentially on the peptide molecule until cleavage occurs.

Figure 10:
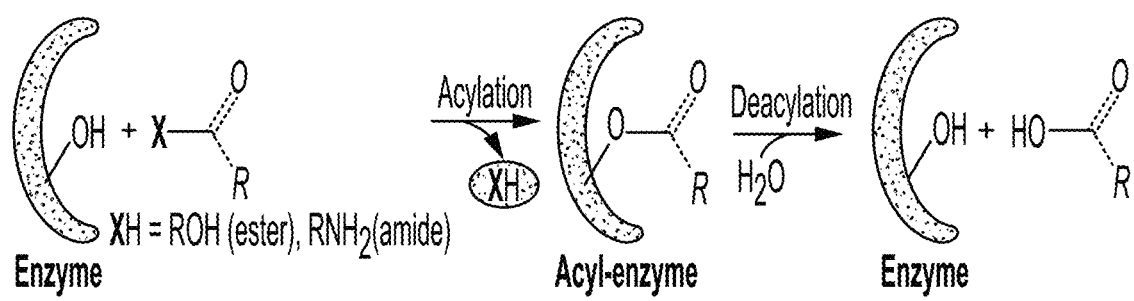
FIG. 10. Schematic presentation of acylation and deacylation steps of an aminopeptidase. For a peptide, the case holds that XH=RNH2 (thus yielding the presence of a peptide bond in the scheme). The N-terminal part of the peptide is symbolized by the moiety in red, whereas the C-terminal part of the peptide is the moiety symbolized by X.

The observation that "on-time" of an enzyme on a substrate can be used to identify said substrate holds especially true for aminopeptidases. Peptidases generally operate through a two-step mechanism (FIG. 10). First, during an acylation reaction the N-terminal moiety of the peptide (for aminopeptidases) or the C-terminal moiety of the peptide (for carboxypeptidases) is cleaved off and covalently linked to the peptidase. Second, in a deacylation reaction the enzyme releases the cleaved amino acid.

An aminopeptidase gains its specificity for particular (groups of) amino acids through a stereo-electronic fit with the transition state of the acylation reaction, impacted among others by the nature of the side chain(s) of the substrate to the N-terminus of the scissile bond. Typically, aminopeptidases have much less binding interactions with the peptide moiety to the C-terminus of the scissile bond, and will thus rapidly dissociate from the peptide (or from the surface to which the peptide was bound) upon the reaction rate-determining acylation or hydrolysis step. If a peptide is immobilized C-terminally from the scissile peptide bond that is cleaved by the peptidase, then upon the acylation reaction, the N-terminal amino acid or amino acid derivative of the peptide will be covalently linked to the enzyme in the case of a serine or cysteine peptidase, or will be non-covalently bound to the enzyme in case of directly hydrolyzing peptidases, whereas the C-terminal moiety will remain conjugated to the surface on which the peptide was immobilized (FIG. 10). Consequently, for selected aminopeptidases, the residence time or the "on-time" on the surface-immobilized peptide substrate is a correlate for the rate of the acylation or hydrolysis step, and hence for the nature of the moiety N-terminal to the scissile bond. The "on-time" of an aminopeptidase can in this case easily be determined by molecularly labelling said aminopeptidase. As such the molecular label acts as a proxy for the "on-time" of the aminopeptidase and thus for the identity of the N-terminal amino acid that is cleaved off by said aminopeptidase. In a particular embodiment of this application, said aminopeptidase can be optically, fluorescently, electrically or plasmonically labelled (see later).

In an alternative embodiment, a solution of aminopeptidase molecules is contacted with the peptide substrate and the residence time/on-time is measured until the N-terminal amino acid (or a derivative thereof) is cleaved off. In such embodiment, the overall residence time of the enzyme in contact with the substrate is measured until such cleavage event, and this value correlates with the inverse of $k_{et}$ of the enzyme for the particular N-terminal amino acid (derivative) on the peptide substrate under the conditions that are used.

For carboxypeptidases from the group of cysteine and serine proteases, the situation is different. More precisely, in case of said carboxypeptidases, the enzyme stays covalently bound to the immobilized peptide moiety after cleaving off the C-terminal amino acid. The carboxypeptidase will not dissociate from the peptide upon the acylation step and it's "on-time" value on the peptide on the immobilization surface will be determined by the rate of the deacylation (hydrolysis) step. The latter hydrolysis step is much less or not informative for the nature of the C-terminal amino acid (which was already released in the solvent during the acylation step). However, in the embodiment where a solution of carboxypeptidase molecules is contacted with the peptide substrate and the residence time/on-time is measured until the C-terminal amino acid (or a derivative thereof) is cleaved off, this value correlates with the inverse of $k_{cat}$ of the enzyme for the particular C-terminal amino acid (derivative) on the peptide substrate under the conditions that are used and such carboxypeptidase can be used in the scope of this invention.

Interestingly carboxypeptidases from the group of metalloproteases do not make this covalent binding and cleave off the C-terminal amino acid by hydrolysis. The "on-time" of said carboxy-metallopeptidases is thus equally informative for the C-terminal amino acid to which it binds and cleaves as aminopeptidases are for the N-terminal amino acids. The use of carboxy-metallopeptidases are thus envisaged as well in the methods described in current application, with the important difference that the polypeptide is then immobilized to a surface through its N-terminus or through a side chain of the peptide. To summarize, besides the utility of isothiocyanate and/or ITC analogues especially useful for this application and the methods disclosed herein are aminopeptidases or carboxy-metallopeptidases. Hence, in various particular embodiments of current application, the cleavage-inducing agent as referred to in the methods and uses in current application is a peptidase, particularly an aminopeptidase or a carboxy-metallopeptidase, more particularly an aminopeptidase.

In particular embodiments of this application, the use is provided of an active peptidase whose rate of cleavage or of which the kinetics of peptidase activity is characteristic for and thus identifies the amino acid substrate, more particularly the terminal amino acid of a polypeptide. One desirable strategy utilizes aminopeptidases, particularly one unique aminopeptidase, more particularly a catalytically active aminopeptidase that recognizes each of the 20 possible N-terminal amino acids. However, it is also envisaged that 2, 3, 4 or more aminopeptidases are utilized that can then distinguish different groups of amino acids, for example but without the purpose of being limited: aromatic amino acids from non-aromatic amino acids, or hydrophobic terminal amino acids, positively charged amino acids, negatively charged amino acids, and small amino acids.

It is also envisaged that by changing the reaction conditions during the experiment (e.g. protein sequencing) the "on-time" value of the aminopeptidase for specific N-terminal amino acids can be changed. This is particularly desirable when the used aminopeptidase has very similar "on-time" values for certain N-terminal amino acids. Therefore, in certain embodiments, the reaction conditions including temperature, pH, solvents among others are adjusted to increase the differentiation between the "on-time" value for amino acid X comparted to the "on-time" value for amino acid Y. In other embodiments, the aminopeptidase itself is engineered to distinguish different amino acids for which the native aminopeptidase has similar residence times. "Engineered" as used herein is a synonym for "synthetic", "recombinant", "man-made" or "non-natural".

As a non-limiting example, the aminopeptidase T from *T. aquaticus* can be used in the methods of the current application (see later). Possible residues to engineer said aminopeptidase are residues within 8 Angstrom radius from the divalent metal ion in the catalytic site, more precisely E250, F252, G315, E316, V317, A318, T336, E340, H345, I346, A347, F348, Q350, Y352, N355, H376, V377, D378 and/or W379. The positions of said residues refer to the positions in the wild-type aminopeptidase T as depicted in SEQ ID No. 7.

Another desirable strategy is that upon binding of the aminopeptidases described in current application, the enzyme "on-time" value can be used to identify the N-terminal amino acids of the immobilized polypeptide. Also envisaged in the application are aminopeptidases, more particularly catalytically active aminopeptidases, uses thereof and methods wherein said aminopeptidases are used, of which the enzyme "on-time" value is instructive or informative for a group or subgroup of amino acids. In certain embodiments, the enzyme "on-time" value will thus classify or categorize an N-terminal amino acid in a group or subgroup of amino acids with a certain probability.

In certain embodiments, the aminopeptidase used in the methods disclosed in the application is an aminodipeptidase, more particularly a catalytically active aminodipeptidase. Aminodipeptidase is a synonym for diaminopeptidase and refers to an enzyme that cleaves off the two most N-terminal amino acids of a polypeptide.

In a preferred embodiment, the aminopeptidase or aminopeptidases used in the methods disclosed in current application are catalytically active. "Catalytically active" means that the aminopeptidase is a fully functional catalytic enzyme. This in contrast to catalytically dead aminopeptidases that have been engineered to bind N-terminal amino acids but without cleaving said N-terminal amino acids, e.g. in WO20140273004.

For the uses and methods described in current application, thermophilic aminopeptidases are especially envisaged. Non-limiting examples of such aminopeptidases that can be used in the methods described in current application are aminopeptidase T from *Thermus aquaticus* (AMPT_THEAQ), aminopeptidase T from *Thermus thermophilus* (AMPT_THET8), PepC from *Streptococcus thermophiles* (PEPC_STRTR), Aminopeptidase S from *Streptomyces griseus* (APX_STRGG), Aminopeptidase from *Streptomyces septatus* TH-2 (Q75V72_9ACTN) and Aminopeptidase 2 from *Bacillus stearothermophilus* (AMP2_GEOSE).

Non-limiting examples of catalytically active aminopeptidases envisaged in the methods of current application and which are disclosed herein are an engineered *Trypanosoma cruzi* cruzipain or cruzain and a *Thermus aquaticus* aminopeptidase T.

In current application, an engineered, catalytically active aminopeptidase comprising a binding domain for any N-terminal amino acid of a polypeptide or for a series of different N-terminal amino acids of a polypeptide is provided, wherein said polypeptide is immobilized on a surface, wherein said aminopeptidase cleaves the N-terminal amino acid upon binding, and wherein the enzyme "on-time" of said aminopeptidase identifies or categorizes said N-terminal amino acid. Also provided herein is an engineered, catalytically active aminopeptidase binding a surface immobilized polypeptide, wherein said aminopeptidase cleaves the N-terminal amino acid of said polypeptide, and wherein the residence time of said aminopeptidase on said N-terminal amino acid identifies or categorizes said N-terminal amino acid.

In a particular embodiment, said polypeptide is immobilized on said surface through a moiety of the peptide C-terminal to the scissile bond. In another particular embodiment, said N-terminal amino acid is a derivatized N-terminal amino acid and said aminopeptidase binds and cleaves said derivatized N-terminal amino acid. In a more particular embodiment, said derivatized N-terminal amino acid is an N-terminal amino acid derivatized with ITC, CITC, SPITC, PITC, azido-PITC or a click-chemistry modified product of azido-PITC (collectively referred to henceforth as 'azido-PITC') and said aminopeptidase binds and cleaves the ITC, CITC, SPITC, PITC or azido-PITC derivatized N-terminal amino acid respectively. "Derivatized" is derived from "derivatization" which refers to a technique used in chemistry or a mechanism of biochemistry which transforms a chemical compound into a product (the reaction's derivate) of similar chemical structure, called a derivative. Generally, a specific functional group of the compound participates in the derivatization reaction and transforms the product to a derivate of deviating, reactivity, solubility, boiling point, melting point, aggregate state, chemical composition, interaction or optical, electrical or plasmonic characteristics. In an alternative embodiment, derivatized means labelled.

In another embodiment, said N-terminal amino acid is selected from the list consisting of Leu, Met, Tyr, Arg, Pro, Gly, Lys, Ala and Val and said binding domain for a series of different N-terminal amino acids or said binding domain for any N-terminal amino acid is a binding domain for a N-terminal acid selected from the list consisting of Leu, Met, Tyr, Arg, Pro, Gly, Lys, Ala and Val. In yet another embodiment, said N-terminal amino acid is Leu, Met, Tyr, Arg, Pro, Gly, Lys, Ala or Val and said binding domain for any N-terminal amino acid is a binding domain for Leu, Met, Tyr, Arg, Pro, Gly, Lys, Ala or Val.

In another particular embodiment, an engineered, synthetic or recombinant aminopeptidase is provided comprising a binding domain for one or more different derivatized or labeled N-terminal amino acid of a polypeptide, wherein said aminopeptidase cleaves said derivatized or labeled N-terminal amino acid upon binding to said derivatized or labeled N-terminal amino acid, and wherein the rate of cleavage of said aminopeptidase or the kinetics of the aminopeptidase activity identifies said N-terminal amino acid. In one embodiment, said derivatized or labeled N-terminal amino acid is an N-terminal amino acid derivatized or labeled with ITC, CITC, SPITC, PITC or azido-PITC. In another embodiment, said derivatized or labeled N-terminal amino acid is a derivatized or labeled Leu, Met, Tyr, Arg, Pro, Gly, Lys, Ala or Val. Said aminopeptidase is thus catalytically active and is not a catalytically dead aminopeptidase.

In one aspect, the application provides an engineered, synthetic or recombinant aminopeptidase comprising an amino acid sequence having a glycine residue at position 25, a serine residue at position 65, a cysteine residue at position 138 and a histidine residue at position 208 of a wild-type *Trypanosoma cruzi* cruzipain or cruzain, wherein the remaining amino acid sequence of said aminopeptidase comprises a sequence having at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of said wild-type *T. cruzi* cruzipain depicted in SEQ ID No. 1 or cruzain depicted in SEQ ID No. 2. This is the same as saying that an engineered aminopeptidase having at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID No. 1 or SEQ ID No. 2 and having a glycine residue at position 25, a serine residue at position 65, a cysteine residue at position 138 and a histidine residue at position 208 is provided. In one embodiment, a cysteine residue is inserted after the first methionine residue of said aminopeptidase. Said cysteine is used to label said engineered cruzipain or cruzain aminopeptidase. In a particular embodiment, said aminopeptidase comprises an amino acid sequence as depicted in SEQ ID No. 3 or SEQ ID No. 4. In a more particular embodiment, said aminopeptidase consists of the amino acid sequence as depicted in SEQ ID No. 5 or SEQ ID No. 6. In particular embodiments, said aminopeptidase of the above aspect and of its embodiments, is a catalytically active aminopeptidase.

The above described specific mutations in the *T. cruzi* cruzipain and cruzain allows activity (binding and cleaving) towards derivatized N-terminal amino acids, more particularly CITC- or SPITC-derivatized N-terminal amino acids. Hence, the methods or current application are also useful to sequence a peptide comprising derivatized amino acids or to identify derivatized N-terminal amino acids. In particular embodiments, said derivatized amino acids are amino acids derivatized with ITC, PITC, azido-PITC, CITC and/or SPITC, even particularly derivatized with CITC and/or SPITC.

Besides the utility of above described engineered *T. cruzi* cruzipain and cruzain that cleaves CITC- or SPITC-derivated N-terminal amino acids in the methods described in current application, said engineered *T. cruzi* cruzipain and cruzain can also be used in the methods described of WO20140273004. In latter document, identification of derivatised N-terminal amino acids is done by a series of N-terminal amino acid binding proteins whereupon the identified N-terminal amino acid is removed by an Edmanase. In case the N-terminal amino acids are derivatised with CITC or SPITC, the engineered *T. cruzi* cruzipain and cruzain described in current application can be used as Edmanase.

In a next aspect, an engineered, synthetic or recombinant aminopeptidase having at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of a wild-type *Thermus aquaticus* aminopeptidase T as depicted in SEQ ID No. 7 is provided, wherein a cysteine residue is inserted after the first methionine residue of said wild-type aminopeptidase. This is the same as saying that an engineered aminopeptidase having at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID No. 7 is provided, wherein a cysteine residue is inserted between the methionine residue at position 1 and the alanine residue at position 2. In a particular embodiment, said aminopeptidase T comprises an amino acid sequence as depicted in SEQ ID No. 8. In a more particular embodiment, said aminopeptidase consists of the amino acid sequence as depicted in SEQ ID No. 8. In particular embodiments, said aminopeptidase of the above aspect and of its embodiments, is a catalytically active aminopeptidase.

As used herein, the terms "identical", "similarity" or percent "identity" or percent "similarity" or percent "homology" in the context of two or more polypeptide sequences, refer to two or more sequences or subsequences that are the same or have a specified percentage of amino acid residues that are the same (e.g., 75% identity over a specified region) when compared and aligned for maximum correspondence over a comparison window or designated region as measured using sequence comparison algorithms or by manual alignment and visual inspection. Preferably, the identity exists over a region that is at least about 25 amino acids in length, or more preferably over a region that is 50-100 amino acids, even more preferably over a region that is 100-500 amino acids or even more in length.

The term "sequence identity" or "sequence homology" as used herein refers to the extent that sequences are identical on an amino acid by amino acid basis over a window of comparison. Thus, a "percentage of sequence homology" is calculated by comparing two optimally aligned sequences over the window of comparison, determining the number of positions at which the identical amino acid occurs in both sequences to yield the number of matched positions, dividing the number of matched positions by the total number of positions in the window of comparison (i.e., the window size), and multiplying the result by 100 to yield the percentage of sequence identity. A gap, i.e., a position in an alignment where a residue is present in one sequence but not in the other is regarded as a position with non-identical residues. Determining the percentage of sequence homology can be done manually, or by making use of computer programs that are available in the art. Examples of useful algorithms are PILEUP (Higgins & Sharp, CABIOS 5:151 (1989), BLAST and BLAST 2.0 (Altschul et al. J. Mol. Biol. 215:403 (1990). Software for performing BLAST analyses is publicly available through the National Center for Biotechnology Information (http://www.ncbi.nlm.nih.gov/). In particular embodiments, the window of comparison to determine the sequence identity of two or more polypeptides (such as aminopeptidases) is the full length protein sequence.

Immobilisation and Labeling

"Immobilization on a surface" as used herein refers to the attachment of one or more polypeptides to an inert, insoluble material for example a glass surface resulting in loss of mobility of said polypeptides. For the methods disclosed in current application, immobilization allows the polypeptide (s) to be held in place throughout the sequencing of the polypeptide or identifying or categorizing the N-terminal amino acid of said polypeptide. The N-terminus should thus be freely accessibly, hence the polypeptide should be immobilized through its C-terminus. Moreover, proteins immobilized onto surfaces with high density allow the usage of small amount of sample solution. Many immobilization techniques have been developed in the past years, which are mainly based on the following three mechanisms: physical, covalent, and bioaffinity immobilization (Rusmini et al 2007 Biomacromolecules 8: 1775-1789; U.S. Pat. No. 6,475,809; WO2001040310; U.S. Pat. No. 7,358,096; US20100015635; WO1996030409). In this application polypeptides are immobilized on glass surfaces using the azide-dibenzocyclooctyl (DBCO) click reaction (see Example 1 and 2) according to protocols available in the art, e.g. Eeftens et al (2015 BMC Biophys 8:9).

In various embodiments of current application, the polypeptide may be immobilized on a surface prior to contact with the aminopeptidase. The peptide may be immobilized on any suitable surface (see later).

Crucial for the methods disclosed in current application is that the polypeptide to be sequenced or of which the N-terminal amino acid is to be identified or categorized is immobilized through the moiety which is most C-terminal of the polypeptide or through the moiety C-terminal of the scissile bond. The polypeptide is thus attached to the surface of the application with its C-terminus or with a moiety along the peptide's structure, C-terminal to the scissile bond (e.g. with a cysteine's thiol function through e.g. maleimide chemistry or gold-thiol bonding, well known in the art).

"Scissile bond" as used herein refers to the covalent chemical bond to be cleaved by one of the aminopeptidases of the application.

"Surface" as used herein is a synonym for carrier or layer. The surface or layer of current application is suitable to use in the detection of molecular labels, electrochemical signals, electromagnetic signals, plasmon related events. Said molecular label can be an optical (comprising but not limited to luminescent and fluorescent labels) or electrical (comprising but not limited to potentiometric, voltametric, coulometric labels) label.

Said layer can also be a multilayer, i.e. a layer that comprises several layers. In case of a multilayer, at least one layer should allow suitable detection of said molecular labels or said electrochemical, electromagnetic or plasmon related events. Therefore, according to particular embodiments, the surface is an active sensing surface. Hence, the surface immobilized polypeptide of said method of sequencing a surface-immobilized polypeptide at single molecule level is a polypeptide immobilized on an active sensing surface. In more particular embodiments, said active sensing surface is either a gold surface or an amide-, carboxyl-, thiol- or azide-functionalized surface on which the polypeptide of said method is chemically coupled. In other particular embodiments, said carrier is a nanoparticle, a nanodisk, a nanostructure, a chip. In most particular embodiments, said surface is a self-assembled monolayer (SAM).

Figure 14:
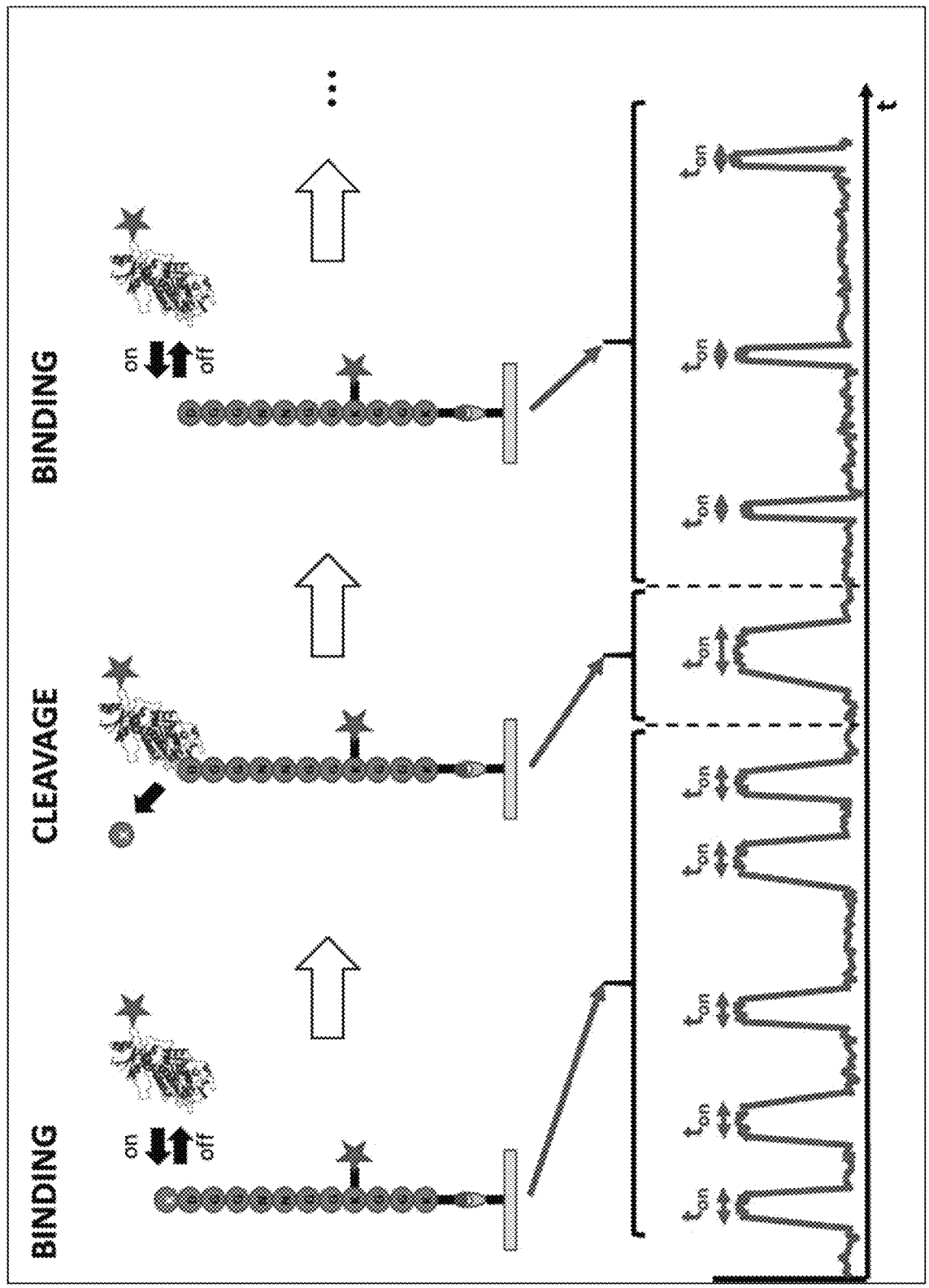
FIG. 14. Monitoring the combination of enzyme-substrate binding events and substrate cleavage events. Single molecule enzyme residence times are monitored with TIRF microscopy by using fluorescently labeled immobilized peptide substrates and free aminopeptidase.

To detect the "on-time" values or residence time, two labelling options can be selected. First, the polypeptides to be sequenced can be labelled for example through their N-terminal amino acids. Alternatively or additionally, internal amino acids can be labelled for example as shown in FIG. 14. The labelling of polypeptides can be done using fluorescent probes, such as but not limited to fluorescamine, o-phthalaldehyde, dansyl chloride and coumarinyl isothiocyanate (CITC). In particular embodiments, the N-terminal amino acid of the immobilized polypeptide of the application is CITC-derivatized or alternatively phrased labeled with CITC. The polypeptides can also be electrically labeled. Electroanalytical methods are a class of techniques by which the presence of an analyte, peptide, enzyme, . . . can be determined by measuring the potential (volts) and/or current (amperes) of the electrical label on the analyte, peptide, enzyme . . . . These methods can be broken down into several categories depending on the label. The three main categories are potentiometry (the difference in electrode potentials is measured), coulometry (the current is measured over time), and voltammetry (the current is measured while the potential is actively altered). There are two basic categories of coulometric techniques. Potentiostatic coulometry involves holding the electric potential constant during the reaction using a potentiostat. The other, called coulometric titration or amperostatic coulometry, keeps the current (measured in amperes) constant using an amperostat. A non-limiting example of an electrical label is sulfophenyl isothiocyanate (SPITC). SPITC is a negatively charged variant of the phenyl isothiocyanate (PITC) probe that is used in MS de novo peptide sequencing for neutralizing N-terminal fragment ions (Samyn et al. 2004 J Am Soc Mass Spectrom 15:1838-1852). In particular embodiments, electrically labeled can be potentiometrically, amperometrically or voltametrically labeled.

In order to detect and measure the "on-time" values or the residence time of the aminopeptidase of the application on the N-terminal amino acid of an immobilized polypeptide or until the N-terminal amino acid of an immobilized polypeptide is cleaved off (see above), said aminopeptidase needs to be detected. The aminopeptidase can interact cleavage-productively or cleavage non-productively with the substrate within the measured residence time until the N-terminal amino acid is cleaved off. Of both interaction types, their length, sum of length and average lengths can be part of the measured residence time relevant to the present invention, as these parameters all are part of the measurement that provides information on how long it takes until the aminopeptidase cleaves off the N-terminal amino acid. The nature of detection is not vital to the invention, as long as the enzyme "on-time" or the residence time of the aminopeptidase can be detected. In certain embodiments of the application, the "on-time" of the aminopeptidase is detected optically, electrically or plasmonically. One way of detecting the aminopeptidases of the application is by fusing it to a molecular label and subsequent detection of the molecular label. Similar to the above, aminopeptidases can be labelled optically, electrically or plasmonically.

Optical detection requires optical labels and includes but is not limited to luminescent and fluorescent detection. The label can thus be a fluorophore. Commercially, there is an extensive catalog of optical labels available, including but not limited to Cy3, Cy5, coumarin, Alexa fluor labels, GFP, YFP, RFP, . . . . In certain embodiments, the label of the aminopeptidase interacts with the label of an immobilized polypeptide or of the N-terminal amino acid of said polypeptide or of the immobilization surface. Said label can be e.g., a fluorophore. In another embodiment, there is at least one molecule in common between the first group and second group of labeled molecules. In one embodiment, the detecting step produces an image, e.g., a fluorescence image (e.g., acquired using Fluorescence Resonance Energy Transfer (FRET), Total Internal Reflection Fluorescence (TIRF), or Zero Mode Waveguide (ZMW)). In another embodiment, the compilation of the images makes a digital profile, e.g., a digital profile that identifies the immobilized polypeptide or its N-terminal amino acids. In particular embodiments, optically labelled is fluorescently labelled. In even more particular embodiments, fluorescent labels are measured or detected through TIRF microscopy.

The binding of an aminopeptidase on the N-terminal amino acids of immobilized proteins and thus a measure for the residence time or "on-time" of the aminopeptidase can also be detected without the need of molecular labels. A non-limiting example of label free electrical detection is the use of field-effect transistor-based biosensors or BioFET. BioFET is a field-effect transistor that is gated by changes in the surface potential induced by the binding of molecules (i.e. aminopeptidase binding on N-terminal amino acids of an immobilized polypeptide). When charged molecules, such as a SPITC labeled aminopeptidase, bind to the FET gate, which is usually a dielectric material, they can change the charge distribution of the underlying semiconductor material resulting in a change in conductance of the FET channel. A BioFET consists of two main compartments: one is the biological recognition element and the other is the field-effect transistor (FET).

BioFETs can be simply constructed from ion-sensitive field-effect transistors (ISFET), silicon nanowires (SiNW), capacitive EIS sensors and light-addressable potentiometric sensors (LAPS) by modifying the gate or coupling it with different biological recognition elements (receptors) (Poghossian and Schöning 2014 Electroanalysis 26: 1197-1213). These include either biomolecular species of various complexity (e.g., enzyme, antibody, antigen, protein, peptide or DNA) or living biological systems (e.g., cell, tissue slice, intact organ or whole organism). For this application, the overall biological recognition system selectively recognizes the aminopeptidase-polypeptide binding or the ITC-polypeptide binding or the ITC analogue-polypeptide binding to be detected and translates the (bio-)chemical information into a chemical or physical signal. The most critical point in information transfer from the biological recognition to the transducer part is the interface between these two domains. In BioFEDs, the potential (or charge) effect is used to transduce these recognizing phenomena. In general, BioFEDs are very sensitive for any kind of charge or potential changes generated by molecular interactions at or nearby the gate insulator/electrolyte interface. The binding of charged species to the gate insulator is analogous to the effect of applying an additional voltage to the gate. Therefore, it can be expected that adsorption or binding of charged biomolecules on the gate surface will modulate the space charge region in the silicon at the insulator/semiconductor interface. This results in a modulation of the drain current of the ISFET, the conductance or current of the SiNWFET, the capacitance of the EIS sensor or the photocurrent of the LAPS. Consequently, by measuring changes in the drain current, of the FETs, conductance of the SiNW, capacitance of the EIS sensor or photocurrent of the LAPS, the aminopeptidase, ITC or ITC analogue "on-time" values can be determined quantitatively. In various embodiments, the detection of aminopeptidases binding to immobilized polypeptides is performed using BioFET or field effect transistor related techniques.

Also, a plasmonic read out can be used to detect the "on-time" of the aminopeptidase of the application or of ITC or ITC analogues. In physics, a plasmon can be defined as a quantum for the collective oscillation of free electrons, usually at the interface between (noble) metals and dielectrics. The term plasmon refers to the plasma-like behavior of the free electrons in a metal under the influence of electromagnetic radiation. Surface plasmons are coherent delocalized electron oscillations that exist at the interface between any two materials where the real part of the dielectric function changes sign across the interface (e.g. a metal-dielectric interface, such as a metal sheet in air). The excitation of surface plasmons which can be done very efficiently with light in the visible range of the electromagnetic spectrum, is frequently used in an experimental technique known as surface plasmon resonance (SPR). In SPR, the maximum excitation of surface plasmons is detected by monitoring the reflected power from a prism coupler as a function of incident angle or wavelength. This technique can be used to observe nanometer changes in thickness, density fluctuations, or molecular absorption and is used for screening and quantifying protein binding events. Commercialized instruments are available that operate on these principles. Therefore, in particular embodiments, the "on-time" of the aminopeptidase of the application or of ITC or ITC analogues is determined by surface plasmon resonance.

Another example by which the "on-time" of the aminopeptidase or of ITC or ITC analogues can be measured is plasmonically enhanced whispering gallery microcavity sensors as was demonstrated for the polymerase DNA interactions (Kim et al 2017 Sci Adv 3:e1603044).

However, notwithstanding the above, it must be clear that the nature of labelling and consequently detection is not vital to the invention, as long as the "on-time" or the residence time of the cleavage-inducing agent can be detected.

Uses of Cleavage Inducing Agents

In another aspect of current application, the use is provided of a cleavage inducing agent to obtain sequence information of a surface-immobilized polypeptide, wherein the residence time of said cleavage inducing agent on a terminal amino acid of said polypeptide identifies said terminal amino acid. In one embodiment, said terminal amino acid is derivatized. In another embodiment, said cleavage inducing agent is isothiocyanate or an isothiocyanate analogue or is a peptidase. More particularly, said isothiocyanate analogue is selected from the list consisting of ITC, CITC, PITC, CITC and azido-PITC. Said peptidase is a catalytically active peptidase, more particularly a catalytically active aminopeptidase.

In yet another embodiment, the use is provided of any of the aminopeptidases described in this application for cleaving the N-terminal amino acid of a polypeptide. In one embodiment, said polypeptide is surface-immobilized. In another embodiment, said cleaving of the N-terminal amino acid of a polypeptide is performed at a single-molecule level. In a particular embodiment, the use of an engineered, synthetic or recombinant aminopeptidase comprising an amino acid sequence having a glycine residue at position 25, a serine residue at position 65, a cysteine residue at position 138 and a histidine residue at position 208 of a wild-type *Trypanosoma cruzi* cruzipain or cruzain, wherein the remaining amino acid sequence of said aminopeptidase comprises a sequence having at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of said wild-type *T. cruzi* cruzipain depicted in SEQ ID No. 1 or cruzain depicted in SEQ ID No. 2 is provided for cleaving the N-terminal amino acid of a polypeptide. Even more particularly, said aminopeptidase provided for cleaving the N-terminal amino acid of a polypeptide has a cysteine residue inserted after the first methionine residue of the wild-type *T. cruzi* cruzipain or cruzain. Even more particularly, said aminopeptidase provided for cleaving the N-terminal amino acid of a polypeptide comprises an amino acid sequence as depicted in SEQ ID No. 3 or in SEQ ID No. 4 or consists of the amino acid sequence as depicted in SEQ ID No. 5 or in SEQ ID No. 6. Most particularly, said cleaving is performed at a single-molecule level and said polypeptide is surface-immobilized, more particularly surface-immobilized through the C-terminus of said polypeptide.

In another particular embodiment, the use of an engineered, synthetic or recombinant aminopeptidase having at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of a wild-type *Thermus aquaticus* aminopeptidase T as depicted in SEQ ID No. 7, wherein a cysteine residue is inserted after the first methionine residue of said wild-type aminopeptidase is provided for cleaving the N-terminal amino acid of a polypeptide. In a more particular embodiment, said aminopeptidase T provided for cleaving the N-terminal amino acid of a polypeptide comprises or consist of an amino acid sequence as depicted in SEQ ID No. 8. Most particularly, said cleaving is performed at a single-molecule level and said polypeptide is surface-immobilized. In other embodiments, said aminopeptidase is a catalytically active aminopeptidase. Also the use is provided of the *T. aquaticus* aminopeptidase T disclosed herein to cleave or to identify the N-terminal amino acid from a surface-immobilized polypeptide, wherein said N-terminal amino acid is selected from the list consisting of Leu, Met, Tyr, Arg, Pro, Gly, Lys, Ala and Val.

In yet another aspect, the use is provided of an aminopeptidase, more particularly a catalytically active aminopeptidase for identifying or categorizing the N-terminal amino acid of a polypeptide or for sequencing a polypeptide. In a particular embodiment, said identification, categorizing or sequencing is done at a single-molecule level. Even more particularly, said polypeptide is surface immobilized through its C-terminus. In one embodiment, said aminopeptidase is labeled, particularly with an optical, electrical or plasmonic label or said aminopeptidase is detected optically, electrically or plasmonically. In a particular embodiment, the use of an engineered, synthetic or recombinant aminopeptidase comprising an amino acid sequence having a glycine residue at position 25, a serine residue at position 65, a cysteine residue at position 138 and a histidine residue at position 208 of a wild-type *Trypanosoma cruzi* cruzipain or cruzain, wherein the remaining amino acid sequence of said aminopeptidase comprises a sequence having at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of said wild-type *T. cruzi* cruzipain depicted in SEQ ID No. 1 or cruzain depicted in SEQ ID No. 2 is provided for identifying the N-terminal amino acid of a polypeptide or for sequencing a polypeptide. Even more particularly, said aminopeptidase provided for identifying the N-terminal amino acid of a polypeptide or for sequencing a polypeptide has a cysteine residue inserted after the first methionine residue of the wild-type *T. cruzi* cruzipain or cruzain. Even more particularly, said aminopeptidase provided for identifying the N-terminal amino acid of a polypeptide or for sequencing a polypeptide comprises an amino acid sequence as depicted in SEQ ID No. 3 or SEQ ID No. 4 or consists of the amino acid sequence as depicted in SEQ ID No. 5 or SEQ ID No. 6. In a particular embodiment, said identification, categorizing or sequencing is done at a single-molecule level. Even more particularly, said polypeptide is surface immobilized through its C-terminus.

In another particular embodiment, the use of an engineered, synthetic or recombinant aminopeptidase having at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of a wild-type *Thermus aquaticus* aminopeptidase T as depicted in SEQ ID No. 7, wherein a cysteine residue is inserted after the first methionine residue of said wild-type aminopeptidase is provided for identifying the N-terminal amino acid of a polypeptide or for sequencing a polypeptide. In a more particular embodiment, said aminopeptidase T provided for identifying or categorizing the N-terminal amino acid of a polypeptide or for sequencing a polypeptide comprises or consist of an amino acid sequence as depicted in SEQ ID No. 8. In a particular embodiment, said identification, categorizing or sequencing is done at a single-molecule level. Even more particularly, said polypeptide is surface immobilized through its C-terminus. In other embodiments, said aminopeptidase is a catalytically active aminopeptidase. In most particular embodiments, said N-terminal amino acid identified using said *T. aquaticus* aminopeptidase T is selected from the list consisting of Leu, Met, Tyr, Arg, Pro, Gly, Lys, Ala and Val.

Methods of the Application

The invention described in current application lies at the basis of several methods which are disclosed below.

In one aspect, a method is provided of identifying or categorizing the terminal amino acid of a surface-immobilized polypeptide, said method comprising:
  a) contacting said surface immobilized polypeptide with a cleavage-inducing agent, wherein said cleavage-inducing agent binds and cleaves the terminal amino acid from said polypeptide;
  b) measuring the residence time of said cleavage-inducing agent on said terminal amino acid;
  c) comparing said measured residence time to a set of reference residence time values characteristic for said cleavage-inducing agent and a set of terminal amino adds;
to identify or categorize said terminal amino acid.

Also a method is provided of obtaining sequence information of a surface-immobilized polypeptide, said method comprising:
  a) contacting said surface-immobilized polypeptide with a cleavage-inducing agent, wherein said agent binds and cleaves the terminal amino acid from said polypeptide;
  b) measuring the residence time of said cleavage-inducing agent on the terminal amino acid of said surface-immobilized polypeptide;
  c) identifying or categorizing said terminal amino acid by comparing said measured residence time to a set of reference residence time values characteristic for said cleavage-inducing agent and a set of terminal amino acids;
  d) allowing said cleavage-inducing agent to cleave off said terminal amino acid;
  e) repeating steps a) through d) one or more times.

In said methods, said residence time is measured optically, electrically or plasmonically. In particular embodiments, said set of terminal amino acids comprises or consists of Leu, Met, Tyr, Arg, Pro, Gly, Lys, Ala and Val.

In various embodiments, said cleavage-inducing agent in said methods is isothiocyanate or an ITC analogue selected from the list consisting of PITC, CITC, SPITC and azido-PITC. In such case, said residence time is the length of time until said terminal amino acid is removed and said terminal amino acid is identified by comparing said length of time to a set of reference values for different amino acids.

In other embodiments, said cleavage-inducing agent in said methods is a peptidase, more particularly a catalytically peptidase, even more particularly a catalytically active aminopeptidase. When an aminopeptidase is used in the methods of current application said polypeptide is surface-immobilized through its C-terminus. In specific embodiments, said step of measuring the residence time of said cleavage-inducing agent on said terminal amino acid in above methods is measuring the residence time of said cleavage-inducing agent on the terminal amino acid until cleavage of the terminal amino acid of said surface-immobilized polypeptide.

Throughout current application, said cleavage-inducing agent can be an aminopeptidase, ITC or ITC analogues. As already discussed herein, the polypeptides immobilized on a surface should be denatured so that the N-terminus is freely accessible (in case the polypeptide is immobilized through its C-terminus) for chemical or enzymatic cleavage but also to avoid steric hindrance or interference of said cleavage. Therefore, the methods of current application are also provided including a first step of polypeptide denaturation. In such denaturing conditions the catalytically active aminopeptidases to be used should withstand the denaturing condition. It is thus preferable that in these cases that said aminopeptidase is a thermophilic and/or solvent resistant aminopeptidase.

In various embodiments, the method herein described are provided wherein said aminopeptidase is any of the aminopeptidase disclosed in the application, more precisely any of the cruzain and cruzipain peptidase from *T. cruzi* or any of the aminopeptidases T from *T. aquaticus* as herein described. In particular embodiments, said methods are provided wherein said N-terminal amino acid is selected from the list consisting of Leu, Met, Tyr, Arg, Pro, Gly, Lys, Ala and Val.

In other embodiments, the method herein described are provided wherein said N-terminal amino acid is derivatized and wherein said cleavage-inducing agent is an aminopeptidase able to cleave derivatized N-terminal amino acids. In more particular embodiments, said N-terminal amino acid is derivatized with CITC or SPITC and the said cleavage-inducing agent is any of the herein disclosed engineered cruzain or cruzipain from *T. cruzi*.

In various embodiments of this application, the methods herein described for identifying or categorizing N-terminal amino acids from a C-terminally immobilized polypeptide or for obtaining sequence information from said polypeptide are methods executed on a single molecule level.

For single molecule measurements, it is envisaged that polypeptides from the methods of current application are immobilized on an active sensing surface. In particular embodiments, said active sensing surface is either a gold surface or an amide-, carboxyl-, thiol- or azide-functionalized surface on which said polypeptide is chemically coupled.

Multiple Measurements of Residence Time and Combined Use with Non-Cleaving Binders In alternative embodiments, the aminopeptidases used in the methods of said application can be aminopeptidases that cleave the N-terminal amino acids only after several rounds of binding and unbinding of the N-terminal amino acids. Every residence time of said aminopeptidases will be informative to determine the residence time until the N-terminal amino acid has been cleaved off, and may help to identify the N-terminal amino acid. In order to detect the time point of change of the identity of the N-terminal amino acid by the aminopeptidase and to predict the N-terminal amino acids more accurately in a single molecule set-up, it is recommended to have multiple measurements for every N-terminal amino acid. This can be achieved by using aminopeptidases that will dock to (association) and undock from (dissociation) the N-terminal amino acid several times before the actual cleavage will occur. It is thus also envisaged that the step of measuring the residence time of catalytically active aminopeptidases in the methods of the application implies the measuring of multiple residence times of said aminopeptidases before said aminopeptidase cleaves the N-terminal amino acid. Alternatively phrased, the methods of the application are provided wherein the residence time of said catalytically active aminopeptidase is measured for every binding event of said aminopeptidase to said N-terminal amino acid. The above is demonstrated in Example 13 and FIG. 14.

In particular embodiments, the methods disclosed in current application are provided wherein the aminopeptidase used in the enzymatic cleavage of the N-terminal amino acids on average has at least 3, at least 4, at least 5, at least 6, at least 7, at least 8, at least 9, at least 10, at least 20 or at least 50 association/dissociation cycles in the time window required for said aminopeptidase to cleave an N-terminal amino acid. This means that at least 3, at least 4, at least 5, at least 6, at least 7, at least 8, at least 9, at least 10, at least 20 or at least 50 cleavage-unproductive association/dissociation cycles occur in between cleavage-productive ones.

Also provided are the methods of current application wherein said surface-immobilized polypeptide is additionally contacted with one or more terminal amino acid binding proteins, wherein the kinetics of the binding events of said one or more binding proteins to said terminal amino acid identify said terminal amino acid. The possibility of using binding specificities of N-terminal amino acid binding proteins to gather information of the substrate is theoretically demonstrated by Rodriques et al (2018, bioRxiv, doi: http://dx.doi.org/10.1101/352310). The additional use of said non-cleavable binders (next to a catalytically active aminopeptidase) in the method of current application can provide additional information in order to predict or identify N-terminal amino acids with a higher accuracy in single molecule experiments. In particular embodiments, said non-cleavable binders have at least 3, at least 4, at least 5, at least 6, at least 7, at least 8, at least 9, at least 10, at least 20 or at least 50 association/dissociation cycles with the N-terminal amino acid in the time window required for the cleavage-inducing agent to cleave said N-terminal amino acid. Said cleavage-inducing agent is an aminopeptidase or ITC or ITC analogues, more particularly said aminopeptidase is one of the aminopeptidases described in current application.

Detection of Cleavage

One of the additional parts of the methods of the application is that the cleavage of the terminal amino acid is to be detected or confirmed. Hence also provided herein are the methods of current application, additionally including a step of determining the cleavage of said terminal amino acid by measuring an optical, electrical or plasmonical signal of the surface-immobilized polypeptide, wherein a difference in optical, electrical or plasmonical signal is indicative for cleavage of said terminal amino acid. Indeed, immobilized peptides with a free N-terminus have several properties which are utilized to determine when an N-terminal amino acid has been cleaved off by the cleaving-inducing agents of the present invention.

In a first example, the free N-terminal amine group carries a positive charge under a broad range of pH. The distance between this positive charge and the anchor point of the peptide, through which it is immobilized, can be measured e.g. by measuring the random telegraph noise (Sorgenfrei et al 2011 Nano Lett 11:3739-3743) in potentiometric detection when the peptide is immobilized on a suitably designed detector element (carbon nanotube, nanometer-scale transistor such as field effect transistor, in particular fin-shaped field effect transistors, gate all-around field effect transistors, nanoribbon field effect transistors and the like). Upon cleavage of an N-terminal amino acid by the cleaving-inducing reagents of the present invention, the positively charged N-terminal amino group comes closer to the anchor point of the peptide and thus to the detector surface. In a fully stretched out peptide, the length with which the distance between this charge and the anchor point shortens is about 3.8 angstrom (contour length), as constrained by the geometry of the covalent bonds in the peptide backbone. Hence, under environmental conditions of peptide secondary structure disruption (high temperature, organic (co-)solvent exposure etc.), the maximum of the distribution of length measurements between the amino-terminal charge and the peptide anchor point has an upper limit which is constrained by the geometry of the covalent bonds in the peptide backbone. Measurement of a change in this maximum length by repeated observation of the peptide's amino-terminal charge during the presence of the cleaving-inducing agent reveals the time point at which the cleavage inducing agent has indeed cleaved off an N-terminal amino acid.

In a second example, the amino-terminal amino acid can be reacted with a reagent in such a way that an amino acid derivative is formed in which the positive charge on the terminal amino-group is eliminated, converted to an amino acid derivative carrying one or more negative charges or increased from a single positive charge to a multiply positive charged amino acid derivative. This can be achieved for example with contacting the immobilized peptide with a suitably chosen N-hydroxysuccinimidyl reagent that carries no charge, one or more positive charges or one or more negative charges). Alternatively, the charge-modulating reagent can be the cleavage-inducing reagent itself, as is the case when the immobilized peptide's terminal amino-group is reacted with a suitably chosen isothiocyanate reagent, such as PITC, CITC, SPITC (4-sulfophenylisothiocyanate) or an azidophenyl isothiocyanate, in which the latter can further be modified through click chemistry on the azide group either prior to the contacting of this agent with the immobilized peptide, during or after the contacting of this agent with the immobilized peptide. In this way, the charge difference between the peptide carrying the amino acid derivative and this peptide after the N-terminal amino acid derivative has been cleaved off is rendered binary (conversion of neutral to positive, conversion of negative to positive or conversion of multiple positive charge to single positive charge) or is enhanced, or both. Using similar detection technology as in Example 1, the time at which the cleavage-inducing agent effectively leads to amino acid cleavage can be measured using a detection of this change in charge.

In a third example, the N-terminal amino acid's amino-group or its side chain can be reacted with an agent that imparts a spectroscopically distinguishable property in such a way that an N-terminal amino acid derivative is generated that can be detected using spectroscopical methods such as fluorimetry, Raman spectroscopy, plasmon resonance etc. In particular, single-molecule detection using total internal reflection fluorescence (TIRF) microscopy is a preferred method, as it is designed to detect fluorescence in a thin layer juxtaposed to the reflective surface, e.g. glass, to which the peptides can be immobilized. Upon contacting the cleavage-inducing agent (which can be e.g. an aminopeptidase, Edmanase or isothiocyanate-containing molecule), the time at which cleavage occurs can be detected by a spectroscopical property change in an observational time series of the immobilized peptide (for example, a loss of fluorescent signal due to cleaving off the fluorescently labeled N-terminal amino acid derivative.

Alternatively, a loss of a Förster Resonance Energy Transfer (FRET) signal can be observed when the immobilized peptide contains a suitable FRET donor or acceptor and the N-terminal amino acid derivative contains a matching FRET acceptor or donor. In yet another embodiment, the N-terminal amino acid is derivatized (e.g. with biotin, for example using a biotinylated isothiocyanate) such that a binding agent (e.g. an avidin such as streptavidin or neutravidin) that carries a spectroscopically distinguishable label (e.g. a fluorophore) can bind the derivatized N-terminal amino acid. The time until cleavage of the N-terminal amino acid can then be measured as the time point at which a change occurs in an observational time series of binding competence of the immobilized peptide to said binding agent. Binding competence is the ability of a peptide to bind or not bind to the binding agent, or the characteristics of such binding, such as binding affinity, $k_{on}$, $k_{off}$. Detection can be done using e.g. TIRF. In yet another embodiment, the N-terminal amino acid is converted into a derivative (e.g. by reaction to an isothiocyanate-containing molecule) to which a binding agent (e.g. a catalytically active or inactive aminopeptidase) that carries a spectroscopically distinguishable label (e.g. a fluorophore) cannot bind. Upon cleavage by the cleavage-inducing agent, such binding agent can then bind to the immobilized peptide and again, the time until cleavage of the N-terminal amino acid can then be measured as the time point at which a change occurs in an observational time series of binding competence of the immobilized peptide to said binding agent.

In yet another embodiment, the time until cleavage by the cleavage-inducing agent can be detected by detecting a change in the binding affinity or binding kinetics of a peptide-binding agent (e.g. a catalytically active or inactive aminopeptidase or Edmanase) to the immobilized peptide. For example, the residence time (time between association and dissociation) of the peptide-binding agent can be measured using any of the techniques described above. Several such cycles of association and dissociation of the peptide-binding agent can be measured and a change in the average residence time can be detected upon cleavage of the N-terminal amino acid. In a particular example, the peptide-binding agent used for detection has a faster association/dissociation kinetics than the time required for the cleavage-inducing agent to induce cleavage of an N-terminal amino acid, such that multiple measurement points of association/dissociation of the peptide-binding agent to the immobilized peptide are typically observable between two cleavage events of N-terminal amino acids. In a particular example, the peptide-binding agent is the same as the cleavage-inducing agent. E.g. a catalytically active aminopeptidase has botch cleavage-productive and cleavage-non-productive association/dissociation cycles. By measuring the affinity and in particular the kinetics of association/dissociation of the aminopeptidase over time during cleavage non-productive peptide binding events, a change is observed in these properties when an N-terminal amino acid is cleaved off and a new N-terminal amino acid is hence displayed for interaction with the aminopeptidase. In a particular embodiment, the aminopeptidase is used under conditions far from the optimal conditions for the enzyme's catalytic rate, such that most association/dissociation events of the aminopeptidase's binding to the immobilized peptide are cleavage non-productive, and changes of the kinetics of these events in the time series of these binding events are used to inform on the time at which the aminopeptidase has cleaved off an N-terminal amino acid.

In yet other aspects, a method is provided of identifying or categorizing the N-terminal amino acid at a single-molecule level of a polypeptide immobilized to a surface through its C-terminus by determining the "on-time" value or the residence time of an aminopeptidase on said N-terminal amino acid, said method comprising contacting said surface immobilized polypeptide with an aminopeptidase and measuring the "on-time" value or the residence time of said aminopeptidase.

In a particular embodiment, said aminopeptidase is any of the aminopeptidases described in this application. Hence, said method is provided wherein said aminopeptidase is an engineered, synthetic or recombinant aminopeptidase comprising an amino acid sequence having a glycine residue at position 25, a serine residue at position 65, a cysteine residue at position 138 and a histidine residue at position 208 of a wild-type *Trypanosoma cruzi* cruzipain or cruzain, wherein the remaining amino acid sequence of said aminopeptidase comprises a sequence having at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of said wild-type *T. cruzi* cruzipain depicted in SEQ ID No. 1 or cruzain depicted in SEQ ID No. 2. Even more particularly, said aminopeptidase provided for said method has a cysteine residue inserted after the first methionine residue of the wild-type *T. cruzi* cruzipain or cruzain. Even more particularly, said aminopeptidase comprises an amino acid sequence as depicted in SEQ ID No. 3 or in SEQ ID No. 4 or consists of the amino acid sequence as depicted in SEQ ID No. 5 or in SEQ ID No. 6. In another particular embodiment, the method of the sixth aspect is provided wherein said aminopeptidase has at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of a wild-type *Thermus aquaticus* aminopeptidase T as depicted in SEQ ID No. 7, wherein a cysteine residue is inserted after the first methionine residue of said wild-type aminopeptidase. In a more particular embodiment, said aminopeptidase T comprises or consist of an amino acid sequence as depicted in SEQ ID No. 8. In other embodiments, said aminopeptidase is a catalytically active aminopeptidase. In most particular embodiments, said N-terminal amino acid to be identified or categorized is selected from the list consisting of Leu, Met, Tyr, Arg, Pro, Gly, Lys, Ala and Val.

In a more particular embodiment, the N-terminal amino acid is derivatized and said aminopeptidase is an aminopeptidase comprising a binding domain for said derivatized N-terminal amino acid and that cleaves said derivatized N-terminal amino acid. In even more particular embodiments, said derivatized N-terminal amino acid is a CITC- or SPITC-derivatized amino acid and said aminopeptidase is able to bind and cleave said CITC- or SPITC-derivatized amino acid. For the latter purpose, said aminopeptidase is specifically engineered. A non-limiting example of such engineered aminopeptidase that binds and cleaves CITC- or SPITC-derivatized N-terminal amino acid is the *T. cruzi* cruzipain or cruzain of the application engineered to have a glycine residue at position 25, a serine residue at position 65, a cysteine residue at position 138 and a histidine residue at position 208.

In yet another aspect, a method of sequencing a surface-immobilized polypeptide at single-molecule level is provided, said method comprising a) contacting said surface-immobilized polypeptide with an aminopeptidase, more particularly a catalytically active aminopeptidase; b) measuring the enzyme "on-time" value of said aminopeptidase; c) identifying or categorizing said N-terminal amino acid by said "on-time" value; repeating the steps a) through c) one or more times. In a particular embodiment, said aminopeptidase is any of the aminopeptidases described in this application. Hence, the methods of the application are provided wherein said aminopeptidase is an engineered, synthetic or recombinant aminopeptidase comprising an amino acid sequence having a glycine residue at position 25, a serine residue at position 65, a cysteine residue at position 138 and a histidine residue at position 208 of a wild-type *Trypanosoma cruzi* cruzipain or cruzain, wherein the remaining amino acid sequence of said aminopeptidase comprises a sequence having at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of said wild-type *T. cruzi* cruzipain depicted in SEQ ID No. 1 or cruzain depicted in SEQ ID No. 2. Even more particularly, said aminopeptidase has a cysteine residue inserted after the first methionine residue of the wild-type *T. cruzi* cruzipain or cruzain. Even more particularly, said aminopeptidase comprises an amino acid sequence as depicted in SEQ ID No. 3 or in SEQ ID No. 4 or consists of the amino acid sequence as depicted in SEQ ID No. 5 or in SEQ ID No. 6. In another particular embodiment, the method of the seventh aspect is provided wherein said aminopeptidase is an engineered, synthetic or recombinant aminopeptidase having at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of a wild-type *Thermus aquaticus* aminopeptidase T as depicted in SEQ ID No. 7, wherein a cysteine residue is inserted after the first methionine residue of said wild-type aminopeptidase. In a more particular embodiment, said aminopeptidase T comprises or consist of an amino acid sequence as depicted in SEQ ID No. 8. In a most particular embodiment, said N-terminal amino acid from said method is selected from the list consisting of Leu, Met, Tyr, Arg, Pro, Gly, Lys, Ala and Val.

In a more particular embodiment, the N-terminal amino acid is derivatized and said aminopeptidase is an aminopeptidase comprising a binding domain for said derivatized N-terminal amino acid and that cleaves said derivatized N-terminal amino acid. In even more particular embodiments, said derivatized N-terminal amino acid is a CITC- or SPITC-derivatized amino acid and said aminopeptidase is able to bind and cleave said CITC- or SPITC-derivatized amino acid. In other embodiments, said aminopeptidase is a catalytically active aminopeptidase.

In another embodiment, the "on-time" values in said method of sequencing a surface-immobilized polypeptide at single molecule level, are measured optically, electrically or plasmonically.

In most particular embodiments of current application, the method as described herein are performed in protein denaturing condition. Said protein denaturing conditions are obtained by high temperature and by the presence of solvents. In particular embodiments, said high temperature is a temperature between 40° C. and 120° C. or between 50° and 110° C. or between 60° C. and 100° C. or between 70° C. and 90° C. In particular embodiments, said solvent is selected from the list consisting of acetic acid, trichloroacetic acid, sulfosalicylic acid, sodium bicarbonate, ethanol, alcohol, cross-linking agents such as formaldehyde and glutaraldehyde, chaotropic agents such as urea, guanidinium chloride, lithium perchlorate, and agents that break disulfide bonds such as 2-mercaptoethanol, dithiothreitol, or tris(2-carboxyethyl)phosphine. Most particularly said solvent is acetonitrile, ethanol or methanol.

In other most particular embodiments of current application, said cleavage-inducing agents are covalent cleavage-inducing agents. In other most particular embodiments of current application, said non-cleavable binders are covalent non-cleavable binders.

The following examples are intended to promote a further understanding of the present invention. While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

EXAMPLES

Figure 2:
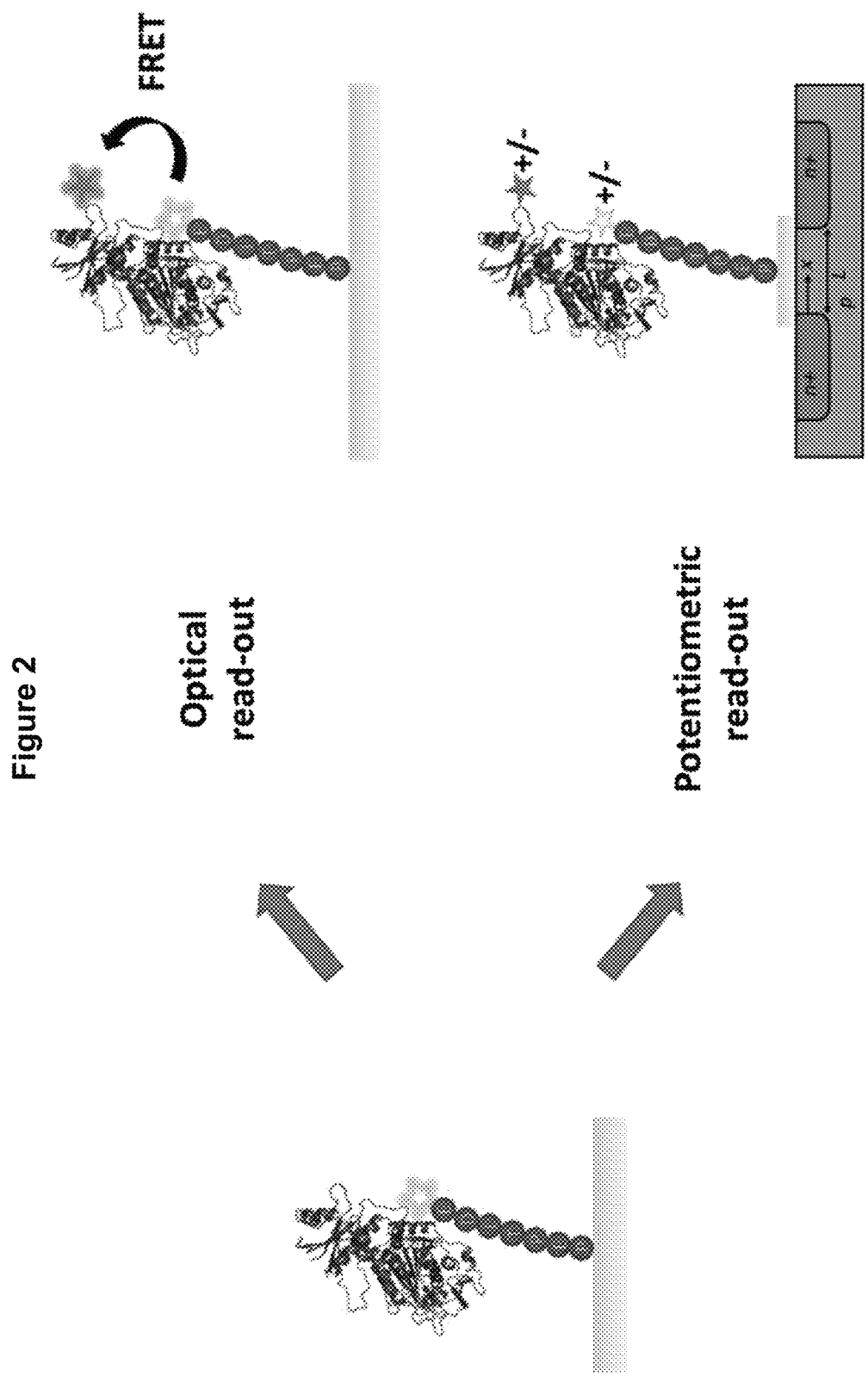
FIG. 2. Schematic representation of non-limiting examples of optical and potentiometric read-out of enzyme residence time.

The peptide sequencing of Havranek and Borgo relies on the use of NAAB's, which are catalytically dead aminopeptidases or t-RNA synthetases. As an alternative for a traditional Edman degradation to cleave of the N-terminal amino acid, an Edmanase enzyme was generated (WO2014273004). This cruzain cysteine protease from *Trypanosoma cruzi* was modified on four positions to be able to bind (and cleave) PITC-derivatized N-terminal amino acids. The first introduced point mutation replacing the catalytic cysteine on position 25 with a glycine (C25G), made the enzyme catalytically incompetent, unless it was rescued by the sulfur atom of a PITC-derivatized peptide substrate. The three additional mutations, i.e. G65S, A138C and L160Y were needed to improve the accommodation of PITC-derivatized substrate. While Havranek and Borgo used catalytically dead NAAB's for amino acid identification and the Edmanase to cleave the N-terminal amino acid after identification, we have developed a method in which surprisingly no catalytically dead NAABs are needed. The method relies entirely on engineered aminopeptidases from which the residence time is informative for the N-terminal amino acid to which it binds and cleaves. The enzymes herein disclosed have an affinity for N-terminally (derivatized) amino acids, regardless of the identity of the N-terminal amino acid. But the enzymes show variability in catalytic efficiency and residence time depending on the identity of the N-terminal amino acid, in order to obtain peptide sequence information (FIG. 1-2). Even more surprisingly we demonstrate a method of identifying N-terminal amino acids comprising correlating solely the residence time of ITC or ITC analogues on said N-terminal amino acids.

Example 1: TIRF Microscopy for Single Peptide Detection

Figure 3:
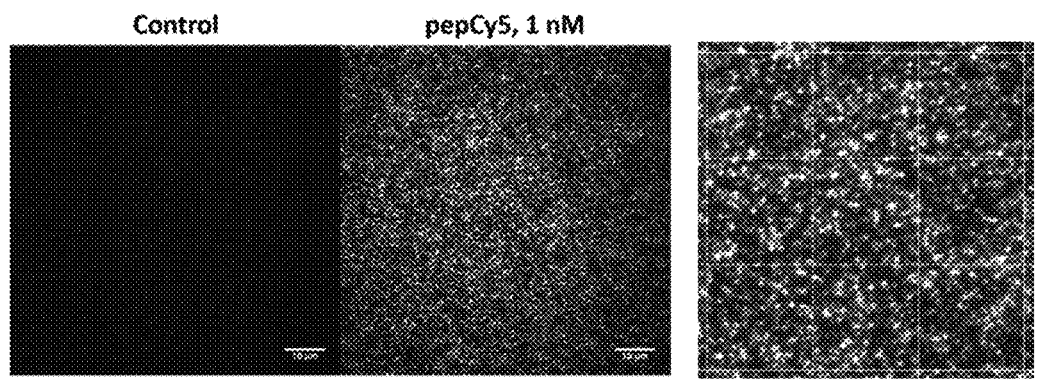
FIG. 3. Immobilization of the Cy5 labeled test peptide (pepCy5) on a glass surface. Left, Control; Middle, pepCy5 at a concentration of 1 nM; Right: zoom image showing the successful spatial distribution.

In a first step, a system was developed to immobilize peptides which are to be sequenced on a surface. Azide-functionalized, oven-cleaned glass plates were used as surface and the peptide NNGGNNGGRGNK to which N-terminally a DBCO-PEG8 group and C-terminally a sulfo-Cy5 fluorescent probe was attached was used as test peptide. The test peptide was immobilized through an azide-DBCO click reaction. The azide-functionalized glass plates were placed on top of 1 ml of 1 nM test peptide, and incubated for 24 h in the dark. For functionalization, 11-azido-undecyl (trimethoxy)silane was used which makes the glass surface hydrophobic, allowing the glass to float on the liquid. After 24 h the glass plates were washed 3 times with 1 ml MS grade water (each 30 min washing). For the control sample, glass plates were incubated with water. Microscopy was executed on a Zeiss TIRF microscope and pictures were taken at $\lambda_{Em}$ 639 nm. The peptides were successfully immobilized on the glass surface, and at a concentration of 1 nM an adequate spatial distribution was obtained (FIG. 3).

Example 2: Trypsin Digestion of Surface Immobilized Peptides

Next, conditions were optimized for enzymatic cleavage of surface immobilized peptides. The test peptide DBCO-PEG8-NNGGNNGGRGNK-Cy5 was again used but now together with trypsin. Successful enzymatic surface reaction is detected after cleavage at the arginine which removes the fluorescent probe. Azide-functionalized, oven-cleaned glass plates were placed on top of 1 ml of 1 nM test peptide and incubated for 24 h in the dark. After washing 3× with MS grade water, glass plates were incubated for 1 h at room temperature with 100 nM trypsin (sequencing grade, promega). Controls were incubated with water. After trypsin treatment, plates were again washed 3× with water. The experiment was also repeated in the presence of 1 µM of DBCO-PEG8-amide passivator (added to the test peptide during the 24 h azide-DBCO click reaction), to evaluate its effect on clustering and aspecific trypsin surface interaction.

Figure 4:
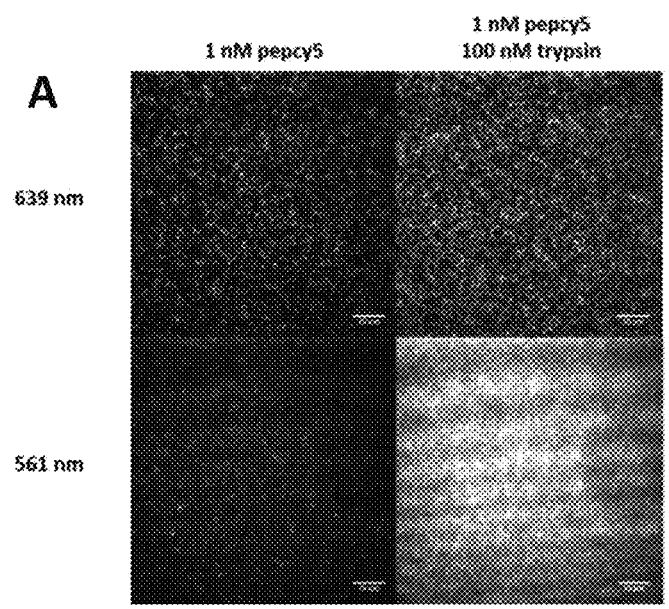
FIG. 4. Trypsin digestion (1 nM) of surface immobilized peptides (1 nM pepCy5). A, The trypsin reaction on immobilized pepCy5 in absence of passivator. B, Trypsin treatment on immobilized pepCy5 in the presence of the passivator dbco-peg8-amide (1 μM). Signal was detected at 639 nm (upper panels) and background was assessed in the lower $\lambda_{Em}$ channel of 561 nm (Cy3 channel) (lower panels).
Figure 4:
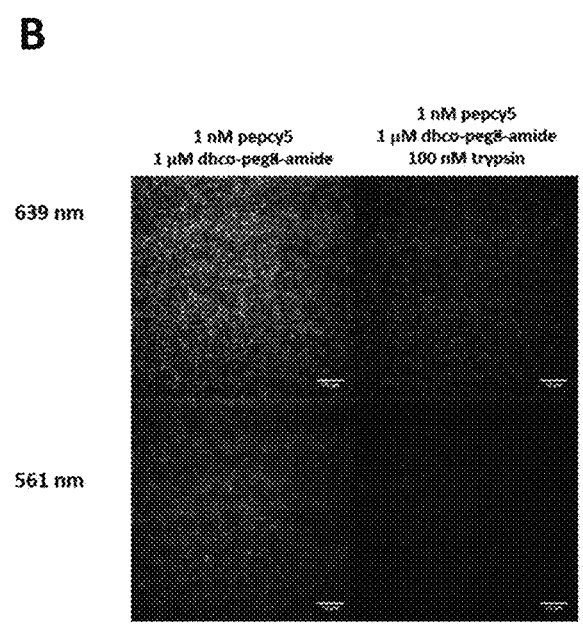

The trypsin reaction in absence of passivator was not successful, due to high background signal from aspecific binding of trypsin on the surface (FIG. 4A). Background was assessed in the lower $\lambda_{Em}$ channel of 561 nm (Cy3 channel). When the passivator was present, the background disappeared, and a considerable amount of immobilized peptide was cleaved, as seen by a significant decrease in spots (FIG. 4B).

Example 3: Peptide N-Terminus Reactive Probes

Depending on the aminopeptidase used (i.e. binding derivatized N-terminal amino acids or binding non-labelled N-terminal amino acids, see Example 4 and further), the immobilized peptides should be labelled or not. The choice of probe will depend on the read-out strategy (FIG. 2). Nonetheless, the probe has to be carefully selected: it needs to be reactive towards the peptide N-terminus, and the derivatized peptide substrate has to fit in the enzyme's catalytic site (see Example 4 for enzyme engineering). Potential fluorescent probe candidates are fluorescamine, o-phthalaldehyde, dansyl chloride and coumarinyl isothiocyanate (CITC) derivates. For charged probes an interesting candidate would be sulfophenyl isothiocyanate (SPITC), a negatively charged variant of the PITC probe, that is used in MS de novo peptide sequencing for neutralizing N-terminal fragment ions (Samyn et al. 2004 J Am Soc Mass Spectrom 15:1838-1852). Although the specificity towards N-terminal primary amines can be increased by carefully controlling the pH (as opposed to lysine primary ε-amines), a certain degree of aspecificity needs to be taken into account, especially when tryptic peptides will be used. Here, the peptides are derivatized with CITC or with SPITC.

Example 4: Edmanase Re-Engineering

In a quest to find an aminopeptidase which is able to bind and cleave any N-terminal amino acid of any peptide, two parallel research lines were explored: one on the use of a re-engineered cruzipain/cruzain cysteine protease from *Trypanosoma cruzi* and one on the use of the *Thermus aquaticus* aminopeptidase T.

Figure 5:
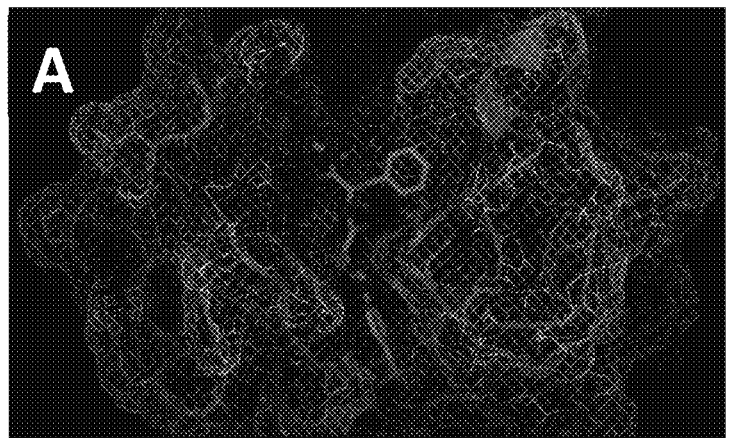
FIG. 5. Successful computational docking of sulfophenyl-Isothiocyanate-Ala-Phe (A) and 3-coumarinyl-isothiocyanate-Ala-Phe (B) on virtually re-engineered Edmanase.
Figure 5:
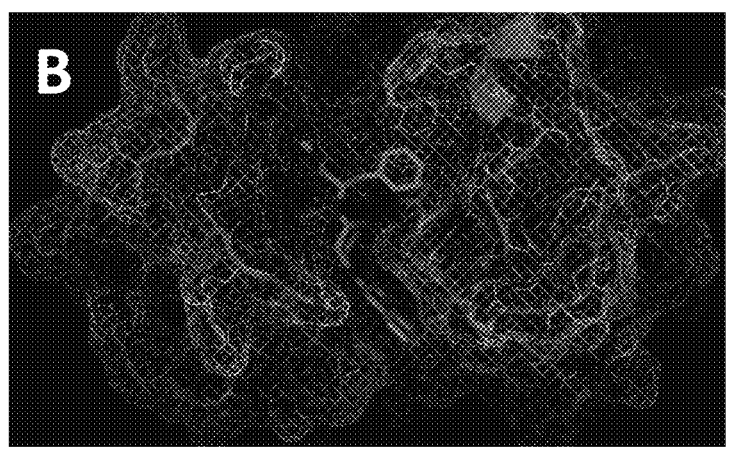
Figure 6:
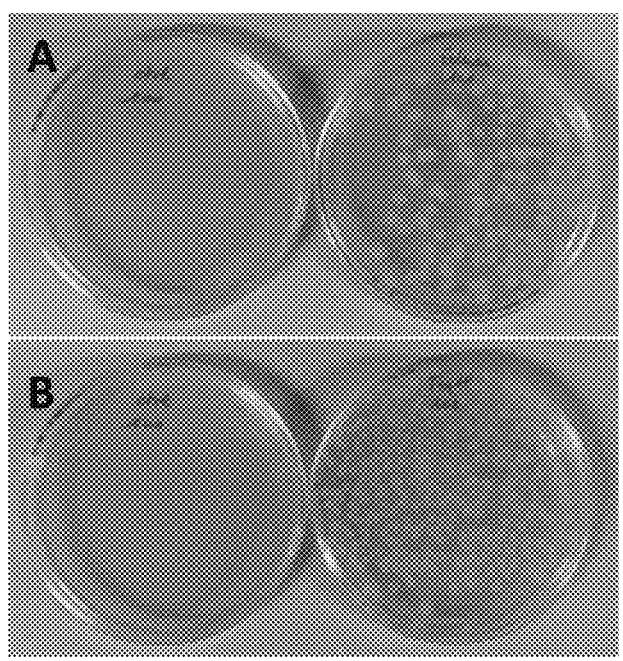
FIG. 6. Successful transformation of the engineered T. cruzi cruzipain (A) and T. aquaticus aminopeptidase T (B) in E. coli BL21.
Figure 7:
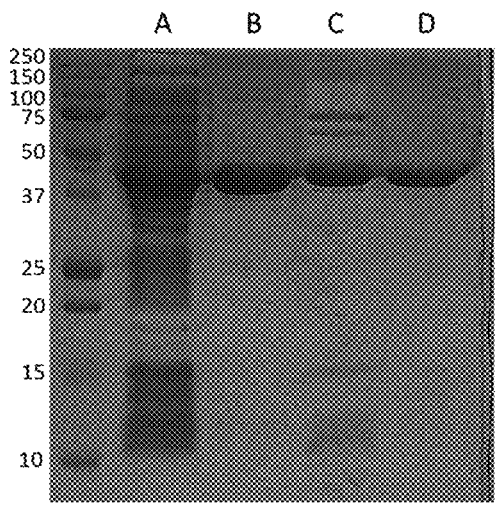
FIG. 7. SDS-PAGE analysis of purified T. aquaticus aminopeptidase T. A, raw soluble fraction; B, Ni-NTA purification; C, heat treatment; D, Ni-NTA purification+heat treatment.
Figure 8:
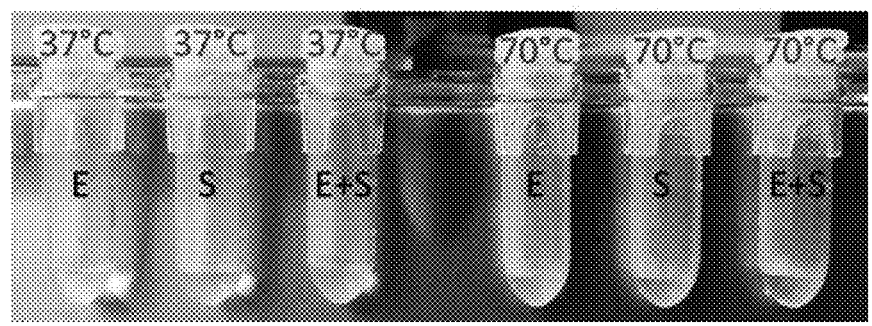
FIG. 8. Peptidase assay with L-leucine-p-nitroaniline. E, enzyme; 5, substrate.

We first re-engineered the cruzain and cruzipain cysteine protease from *Trypanosoma cruzi* to be able to bind derivatized N-terminal amino acids, more precisely to CITC-derivatized and SPITC-derivatized N-terminal amino acids. Computational docking (AutoDock-Vina; Trott and Olsen 2010 J Comput Chem 31:455-461) of fluorescent or charged isothiocyanate probes on the cruzain or cruzipain enzyme and virtual mutants gave several potential re-engineering options. SPITC-Ala-Phe successfully docked on said cruzain and cruzipain when Tyr160 was renatived into Leu (FIG. 5A). The nearby Glu208 could result in a charge clash with SPITC's sulphate but could be avoided by virtually mutating it to a His. By doing so, an re-engineered *T. cruzi* cruzain and cruzipain was developed comprising four point mutations (i.e. C25G, G65S, A138C, E208H) on which fluorescent 3-CITC-Ala-Phe, as well as its 5-, 6-, 7- and 8-coumarinyl analogues, yielded overall correct docking poses within the groove of the active site (FIG. 5B).

Example 5. *E. coli* BL21(DE3) Transformation with *T. cruzi* Cruzipain_pET24b(+)

In a next step, the engineered cruzipain (C25G, G65S, A138C, E208H) was recombinantly produced. A codon-optimized DNA sequence encoding the re-engineered cruzipain was cloned into the pET24b(+) plasmid (NdeI-BamHI). A Cys was added at the N-terminus of the protein and a 6×His was added at the C-terminus. The full length protein has a molecular weight of ±37.5 kDa and an estimated pI of 5.7. Its sequence is depicted in SEQ ID No. 5:

```
MCAPAAVDWRARGAVTAVKDQGQCGSGWAFSAIGN
VECQWFLAGHPLTNLSEQMLVSCDKTDSGCSSGLM
NNAFEWIVQENNGAVYTEDSYPYASGEGISPPCTT
SGHTVGATITGHVELPQDEAQIAAWLAVNGPVAVC
VDASSWMTYTGGVMTSCVSEQLDHGVLLVGYNDSA
AVPYWIIKNSWTTQWGEEGYIRIAKGSNQCLVKEH
ASSAVVGGPGPTPEPTTTTTTSAPGPSPSYFVQMS
CTDAAQVGCENVTLPTGQCLLTTSGVSAIVTCGAE
TLTEEVFLTSTHCSGPSVRSSVPLNKCNRLLRGSV
EFFCGSSSSGRLADVDRQRRHQPYHSRHRRLHHHH
HH
```

Successful transformation of the re-engineered cruzipain was obtained (FIG. 6A). Next, the kinetics of the re-engineered cruzipain were assayed with synthetic SPITC- and CITC-derivatized 7-amino-4-methylcoumarin (AMC) amino acid analogues. Upon removal of the SPITC- or CITC-derivatized N-terminal amino acid, the fluorogenic AMC is released and detected. Using computer simulations, the kinetics data are then be used to assess the viability of using the enzyme "on-time" values for sequencing peptides.

Example 6: *E. coli* BL21(DE3) Transformation with *T. aquaticus* aminopeptidaseT_pET24b(+)

A codon-optimized DNA sequence encoding the aminopeptidase T from *Thermus aquaticus* (Taq-APT or TaqAPT from hereon) was synthesized. The Taq-APT gene was then cloned into the pET24b(+) plasmid (NdeI-BamHI) (FIG. 9). A Cys was added at the N-terminus and a 6×His was added at the C-terminus. The full length protein has a molecular weight of ±45.7 kDa and an estimated pI of 5.6. Its sequence is depicted in SEQ ID No. 8:

```
MCDAFTENLNKLAELAIRVGLNLEEGQEVATAPIE
AVDFVRLLAEKAYENGASLFTVLYGDNLIARKRLA
LVPEAHLDRAPAWLYEGMAKAFHEGAARLAVSGND
PKALEGLPPERVGRAQOAQSRAYRPTLSAITEFVT
NWTIVPFAHPGWAKAVFPGLPEEEAVQRLWQAIFQ
ATRVDQEDPVAAWEAHNRVLHAKVAFLNEKRFHAL
HFQGPGTDLTVGLAEGHLWQGGATPTKKGRLCNPN
LPTEEVFTAPHRERVEGVVRASRPLALSGQLVEGL
WARFEGGVAVEVGAEKGEEVLKKLLDTDEGARRLG
EVALVPADNPIAKTGLVFFDTLFDENAASHIAFGQ
AYAENLEGRPSGEEFRRRGGNESMVHVDWMIGSEE
VDVDGLLEDGTRVPLMRRGRWVIHHHHHH
```

Successful transformation of the re-engineered Taq-APT was obtained (FIG. 6B).

Example 7: Taq-APT Expression and Purification

The recombinant expression of Taq-APT in *E. coli* BL21 (DE3) transformants was verified and optimized. Here, the purification of the (thermophilic) protein is tested with Ni-NTA spin columns or heat treatment, or the combination of both. An aliquot of BL21(DE3) pET-24b(+)-Taq-APT transformed cells was added to 5 ml of LB+50 μg/ml kanamycin, grown overnight at 37° C. and diluted 100× in 5 ml fresh LB+50 μg/ml kanamycin. After 2 h incubation at 37° C. and induction with 1 mM IPTG was performed where after the cultures were grown overnight at 28° C. Cell were collected (4,000×g for 10 min), resuspended in 1 ml PBS+10 mM imidazole (pH 7.5-8), sonicated (is on, is off, 90 sec, 30% amplitude) and centrifuged at full speed for 5 min. The supernatant was collected and split up in 4×200 μl for testing 4 different conditions: (A) Raw soluble fraction, (B) Ni-NTA purification, (C) Heat treatment and (D) Ni-NTA purification+heat treatment. After treatments, samples were concentrated with 10 kDa spin columns to a volume of about 50 μl. From this, 10 μl was mixed with 10 μl SDS sample buffer, and samples were analyzed with SDS-PAGE (FIG. 8). For details on the Ni-NTA purification protocol see Experimental procedures. Purification through heating was done at 80° C. for 30 min.

The combination of Ni-NTA and heating resulted in an acceptably pure Taq-APT extract (FIG. 7). A peptidase assay with L-leucine-p-nitroaniline (140 μl PBS buffer, 10 μl 24 mM L-leucine-p-nitroaniline in MeOH and 10 μl purified Tag-APT) confirmed the presence of the active (amino) peptidase, with thermophilic properties (activity at Taq optimum of 70° C.) (FIG. 8).

Example 8. Determination of Kinetic Parameters of *T. aquaticus* Aminopeptidase T The kinetic parameters from *T. aquaticus* aminopeptidase T for cleaving different amino acid substrates was determined with a p-nitroanilide assay. Substrates consist of an N-terminal amino acid with a p-nitroanilide attached to its C-terminus. Upon amino acid cleavage, the free nitroanilide can be monitored by measuring the absorbance at 405 nm. *T. aquaticus* aminopeptidase T as depicted in SEQ ID No 8 was added in a concentration of 2.0625 µM (in PBS) to different concentrations of amino acid p-nitroanilide substrate (0.0625, 0.125, 0.25, 0.5, 1 and 2 mM in PBS). Subsequently p-nitroanilide release was continuously measured at 40° C. with a FLUOstar Omega microplate reader (MBG LabTech). From this, the initial velocity of the reaction at each substrate concentration was derived ($v_0$). For each amino acid, a Lineweaver-Burke plot was generated from which the reaction $V_{max}$ and enzyme-substrate $K_M$ was determined. The turnover number, $k_{cat}$, was calculated from the $V_{max}$ and the enzyme concentration ($k_{cat}$=Vmax/[E]). The enzyme on-time value was then calculated by taking the reciprocal from the $k_{cat}$ value. Kinetic parameters for nine amino acids are listed in Table 1. The "on-time" values as shown in Table 1 are calculated as $1/k_{cat}$ and as such is the overall time needed for an enzyme solution on the peptide until catalysis occurs.

TABLE 1

Kinetic parameters of the p-nitroanilide assay using nine different amino acids, including the on-time of *T. aquaticus* aminopeptidase T for said nine different amino acids.

|     | $K_M$ (mM) | $k_{cat}$ ($s^{-1}$) | $k_{cat}/K_M$ ($mM^{-1}s^{-1}$) | on-time (s) | on-time (min) |
| --- | --- | --- | --- | --- | --- |
| Leu | 0.092 | 0.00256 | 0.02795 | 390 | 6.5 |
| Met | 0.099 | 0.00471 | 0.04778 | 212 | 3.5 |
| Tyr | 0.211 | 0.00707 | 0.03356 | 142 | 2.4 |
| Arg | 0.415 | 0.01638 | 0.03942 | 61 | 1.0 |
| Pro | 0.546 | 0.00198 | 0.00363 | 504 | 8.4 |
| Gly | 0.765 | 0.00307 | 0.00401 | 326 | 5.4 |
| Lys | 0.193 | 0.00148 | 0.00766 | 677 | 11.3 |
| Ala | 0.736 | 0.01167 | 0.01586 | 86 | 1.4 |
| Val | 0.192 | 0.00138 | 0.00716 | 727 | 12.1 |

The assays were performed at 40° C. below the enzyme's temperature optimum. Working more closely to the optimal temperature of 70° C. speeds up the reaction speed ($k_{cat}$ and enzyme on-time). In conclusion, we surprisingly found that the *T. aquaticus* aminopeptidase T as herein described is able to bind and cleave nine different amino acids with differential kinetics. Moreover the kinetics of the reactions are linked to the identity of the amino acid and even more surprisingly the spread of the $k_{cat}$ values of the different amino acids allows to differentiate between and hence identify the different amino acids. The results as shown here not only validate the utility of the aminopeptidases as disclosed herein but also underpin and substantiate the methods and uses disclosed in current application.

Example 9. Activity of *T. aquaticus* Aminopeptidase T Towards Different Amino Acid p-Nitroanilide Substrates at 40° C. and 80° C.

Figure 11:
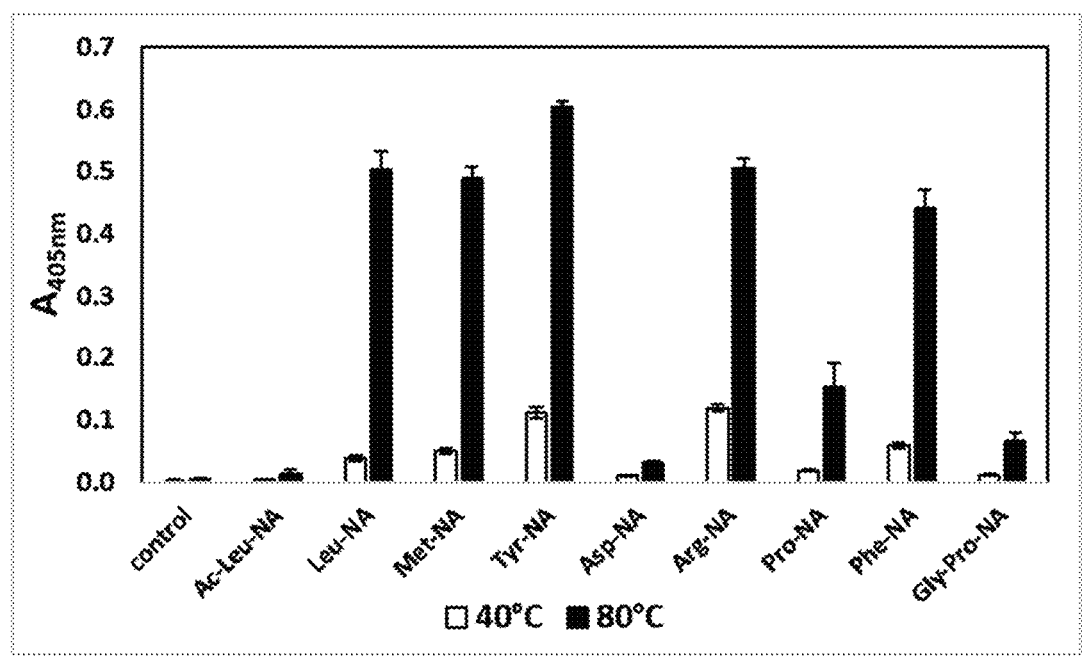
FIG. 11. Aminopeptidase assay with different amino acid p-nitroanilide substrates. Enzyme and substrate (1.5 mM) were incubated for 2 h at 40° C. or 80° C. in PBS, after which the released p-nitroanilide was quantified by measuring the absorbance at 405 nm.

The TaqAPT enzyme shows activity towards all amino acid p-nitroanilide substrates in the current test panel. As described herein and in line with the invention described in current application, the activity differs between different amino acids. At 80° C., the panel of amino acid substrates can be roughly divided in fast-cleaved (L, M, Y, R, F) and slow-cleaved (D, P) substrates. However, at 40° C. it seems like the panel is divided in fast-cleaved (Y, R) and slow-cleaved (D, P), and substrates that lie in between (L, M, F). At 40° C., activity shows roughly a 10× to 3× reduction in activity, depending on the N-terminal amino acid. Finally, TaqAPT is not only active in the p-nitroanilide assay. More importantly the inventors demonstrated that the TaqAPT also cleaves peptide substrates. For example in FIG. 11 it is shown that TaqAPT cleaves dipeptides even with a proline at the second position. The N-terminal amino acid from peptides with proline at the second position is not easily cleaved since peptide bonds adjacent to the amino acid proline are resistant to cleavage by most peptidases (Iyver et al. 2015 FEBS Open Bio. 2015 Apr. 2; 5:292-302). In contrast to what is stated in Minagawa et al (1988 Agricultural and Biological Chemistry 52:1755-1763) we show here that *T. aquaticus* aminopeptidase T can cleave N-terminal amino acids even when proline is at the second position. This surprising finding greatly enhances the generic use of Taq-APT in the method and uses disclosed in current application and in single molecule peptide sequencing in general.

Example 10. Organic Solvent Tolerance of Aminopeptidase T from *T. aquaticus*

Figure 12:
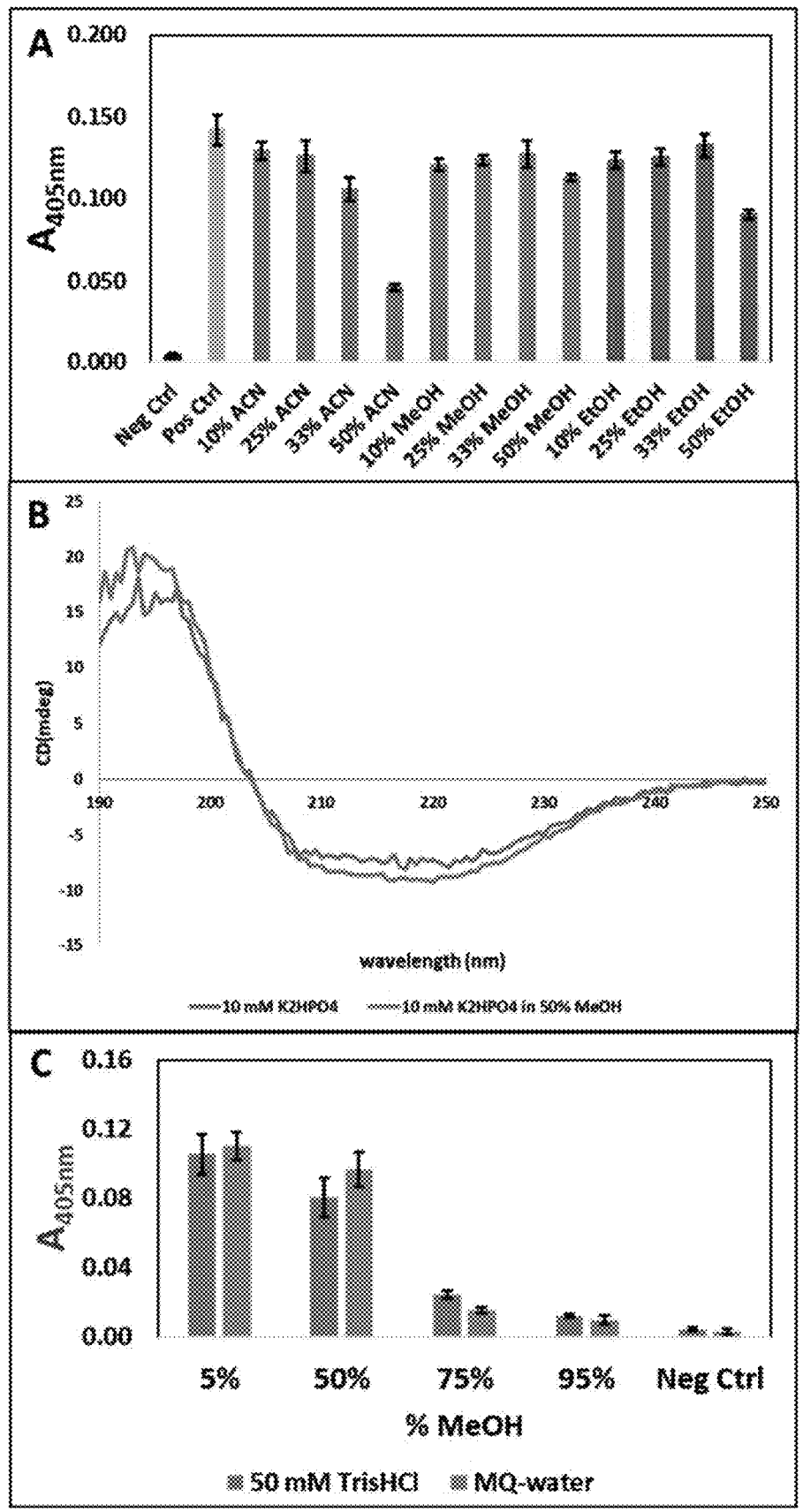
FIG. 12. Organic solvent tolerance of aminopeptidase T from T. aquaticus. A. The activity of aminopeptidase T was measured with L-leucine-p-nitroanilide substrate. Enzyme and substrate were incubated for 3 h at 40° C. in 50 mM TrisHCl (pH 8) containing different concentrations of the organic solvents acetonitrile (ACN), methanol (MeOH) and ethanol (EtOH). B. Circular dichroism analysis of aminopeptidase T secondary structure in 0% versus 50% MeOH (in 10 mM dipotassium phosphate buffer ($K_2HPO_4$)). C. Enzyme activity in varying concentrations of MeOH in buffer (50 mM TrisHCl, pH 8) versus deionized water (MilliQ).

For single peptide detection of surface-immobilized polypeptide, it is crucial that said polypeptides are completely denatured and do not have any secondary structure anymore. It is well-known in the art that this can be achieved by solvents (such as methanol) or high temperatures. When these harsh conditions are needed, the aminopeptidases used should tolerate solvents and/or high temperatures. Next to demonstrating that TaqAPT is active at temperature of 80° C., we also investigated whether the aminopeptidase from *T. aquaticus* described herein is tolerant towards organic solvents. As shown here, the aminopeptidase T from *T. aquaticus* remains completely active up until 50% methanol, 33% acetonitrile and 33% ethanol, which demonstrates that the enzyme is quite tolerant for organic solvents (FIG. 12A). At higher organic solvent concentrations, activity can still be detected, albeit lower. When analyzing the enzyme with circular dichroism (CD) in 0% methanol versus 50% methanol, no structural differences were observed (FIG. 12B). Furthermore, the enzyme appears to be fully active in deionized (MS grade) water, which might be advantageous when the enzyme will be used with ultra-sensitive chip technology (e.g. electrical biosensor such as field effect transistors) (FIG. 12C).

Example 11. Site-Specific N-Terminal Labeling of Aminopeptidase T from *T. aquaticus*

Figure 13:
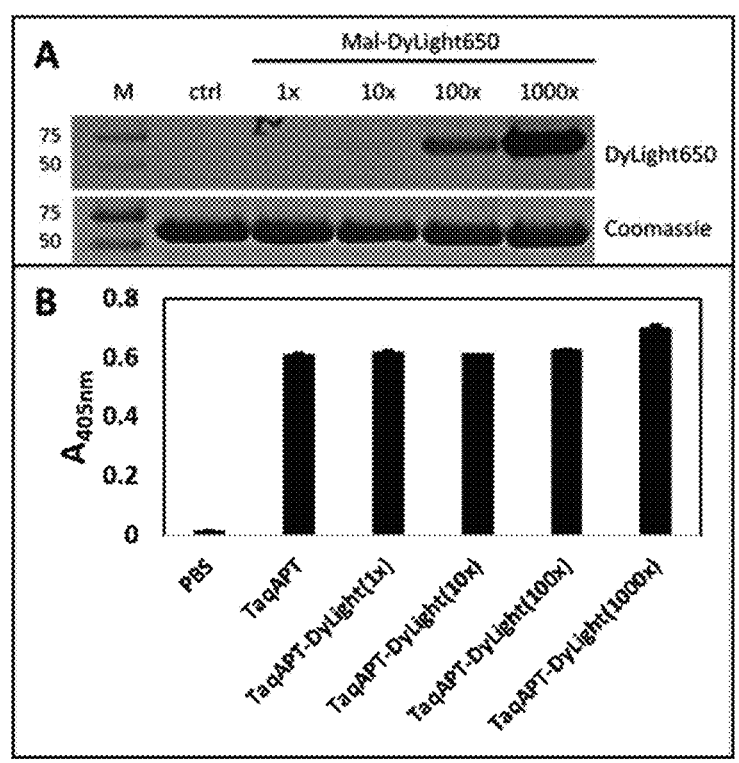
FIG. 13. Site-specific fluorescent labeling of aminopeptidase T. A. SDS-PAGE analysis of aminopeptidase T after labeling the N-terminal cysteine with an equimolar and a 1×, 10×, 100× and 1000× molar excess of maleimide-DyLight650. Aminopeptidase T was visualized with fluorescence (DyLight650 label) and coomassie (total protein). B. Aminopeptidase T activity check with L-leucine-p-nitroanilide after labeling with maleimide-DyLight650.

Recombinant Taq aminopeptidase T, containing an extra N-terminal cysteine, was incubated overnight with the fluorescent maleimide-DyLight650 probe in the presence of the reducing agent TCEP (10 mM). Maleimide-DyLight650 was added in equimolar concentration, and in 10×, 100× and 1000× excess molar concentration. After separating the aminopeptidase with SDS-PAGE, it was visualized using a Coomassie stain, as well as with fluorescence to evaluate protein labeling with DyLight650. FIG. 13A shows that the aminopeptidase is labeled with DyLight650. Moreover, a L-leucine-p-nitroanilide assay demonstrated that labeling the aminopeptidase does not jeopardize its function (FIG. 13B).

Example 12. Aminopeptidase Labelling

For the read-out of the sequencing steps and thus to detect the enzyme "on-time" values, two sensor options are used:

optical and potentiometric (FIG. 2). An optical labelling of the aminopeptidase was shown in Example 11. An alternative optical read-out strategy with fluorescent probes can be on the aminopeptidase as well as on the peptide substrate for measuring the on-time with fluorescent resonance energy transfer (FRET) and for detecting a successful cleavage event.

Considering that the concept is single-molecule based, a predictable and specific labeling of the enzyme is required. In order to have a reasonable coverage of the human proteome, up to $10^9$ reads are required (e.g. 10,000 expressed proteins with dynamic range of $10^4$ and requiring at least 10 reads of the least abundant protein) (Geiger et al. 2012 Mol Cell Proteomics 11:M111.014050). Single molecule detection can be accomplished with zero mode waveguides (ZMW), such as those used in single molecule DNA sequencing according to Rhoads and Au (2015 Genomics Proteomics Bioinformatics 13:278-289). Potentiometric read-out on the other hand requires charged probes as to influence the field-effect transistor (FET) voltage potential.

For site-specific labeling of the aminopeptidases a one-step chemical modification at the enzyme N-terminus is performed. The enzyme is specifically modified at the N-terminal primary amine with pyridine carboxyaldehyde derivates as in MacDonald et al. (2015 Nat Chem Biol 11:326-331). The cysteine which was added in both aminopeptidase (see Example 5 and 6) is specifically modified with aldehyde-probes, or with maleimide-probes when no other (surface-exposed) cysteines are present (Gunnoo and Madder 2016 Chembiochem 17:529-553). For potentiometric on-time measurement, the need for adding charges to the enzyme depends on its isoelectric point (pI). If needed, the enzyme's net charge can be altered by introducing charged probes through (site-specific) modification, or through the unilateral neutralizing of positively or negatively charged residues (e.g. lysine formylation).

Example 13. Single Molecule Peptide N-Terminal Amino Acid Identification or Categorization by Measuring Aminopeptidase Residence Time The use of the aminopeptidase T from *T. aquaticus* was further validated in an independent experimental set-up. A series of synthetic peptide substrates with identical primary structure except for the N-terminal amino acid are immobilized where after the residence times of labeled aminopeptidase T from *T. aquaticus* are measured using TIRF microscopy. The peptide substrates have the following overall structure: X-DGGNNGGK(fluo)GGK(dbco/mal/nhs), in which the C-terminal lysine has a DBCO, maleimide or N-hydroxysuccinimide group attached to its side chain, for immobilizing the substrate on a surface. A second lysine has a fluorescent group attached to its side chain for pinpointing the single molecule substrates on that surface. The N-terminus will have a variable amino acid or a varying sequence of amino acids (X), that is proceeded by an aspartic acid residue which serves as reaction brake, considering the very low activity of aminopeptidase T from *T. aquaticus* towards this residue.

After immobilizing the peptide substrates and determining the single molecule substrate locations in the field-of-view, the fluorescently labeled aminopeptidase is added and the consecutive enzyme residence times on the substrate locations is measured. Considering that both the enzyme-substrate binding kinetics ($K_M$) and the substrate cleavage kinetics ($k_{cat}$) depend on the identity of the N-terminal amino acid, by measuring the number of enzyme-substrate 'on-off' events and the overall time until substrate cleavage, the identity of the N-terminal amino acid is derived or categorized (FIG. 14). Verification of substrate cleavage is derived from a measurable change in frequency of enzyme-substrate 'on-off' events before and after cleavage (FIG. 14 below). When using a thermophilic aminopeptidase (e.g. *T. aquaticus* aminopeptidase T) at a far-below optimal temperature, cleave kinetics are significantly reduced leading to an increase in the number of enzyme-substrate 'on-off' events.

As it is described in the detailed description of current application, a single aminopeptidase can be used for capturing both the 'on-off' events on the N-terminal amino acid, as well as for cleaving the N-terminal amino acid. Alternatively, also a combination of two different aminopeptidase enzymes can be used, or a combination of an aminopeptidase and a chemical N-terminal amino acid binder/cleaver (see description).

Example 14. Edman Degradation Reaction Kinetics is Dependent on the N-Terminal Amino Acid Residue Next, we surprisingly found that the Edman degradation chemistry can be adapted for the sequencing of immobilized peptides at the single molecule level. First, proteins are immobilized on a surface through their C-terminus, after which amino acids are continuously cleaved off via Edman degradation chemistry. While the N-terminal coupling of the Edman reagent is independent of the identity of the N-terminal amino acid, the speed of the cleavage reaction depends on it. So by monitoring the cleavage reaction time on each subsequent N-terminal amino acid, sequence information can be obtained. To circumvent the issue with N-terminal modifications, the immobilized proteins are first proteolyzed (for example with trypsin), leaving C-terminal polypeptides behind with free, accessible N-termini. By using a traceable ITC agent, the chemical reaction time can hereby be monitored. For example, sulfophenyl isothiocyanate carries a negative charge, useful in electrical measurements. Or azidophenyl isothiocyanate can be used which can be labeled through click chemistry (charged group, fluorescent probe). Finally, the reaction can be performed in high organic solvent, enabling thorough structure denaturation, and allowing reaction control.

Figure 16:
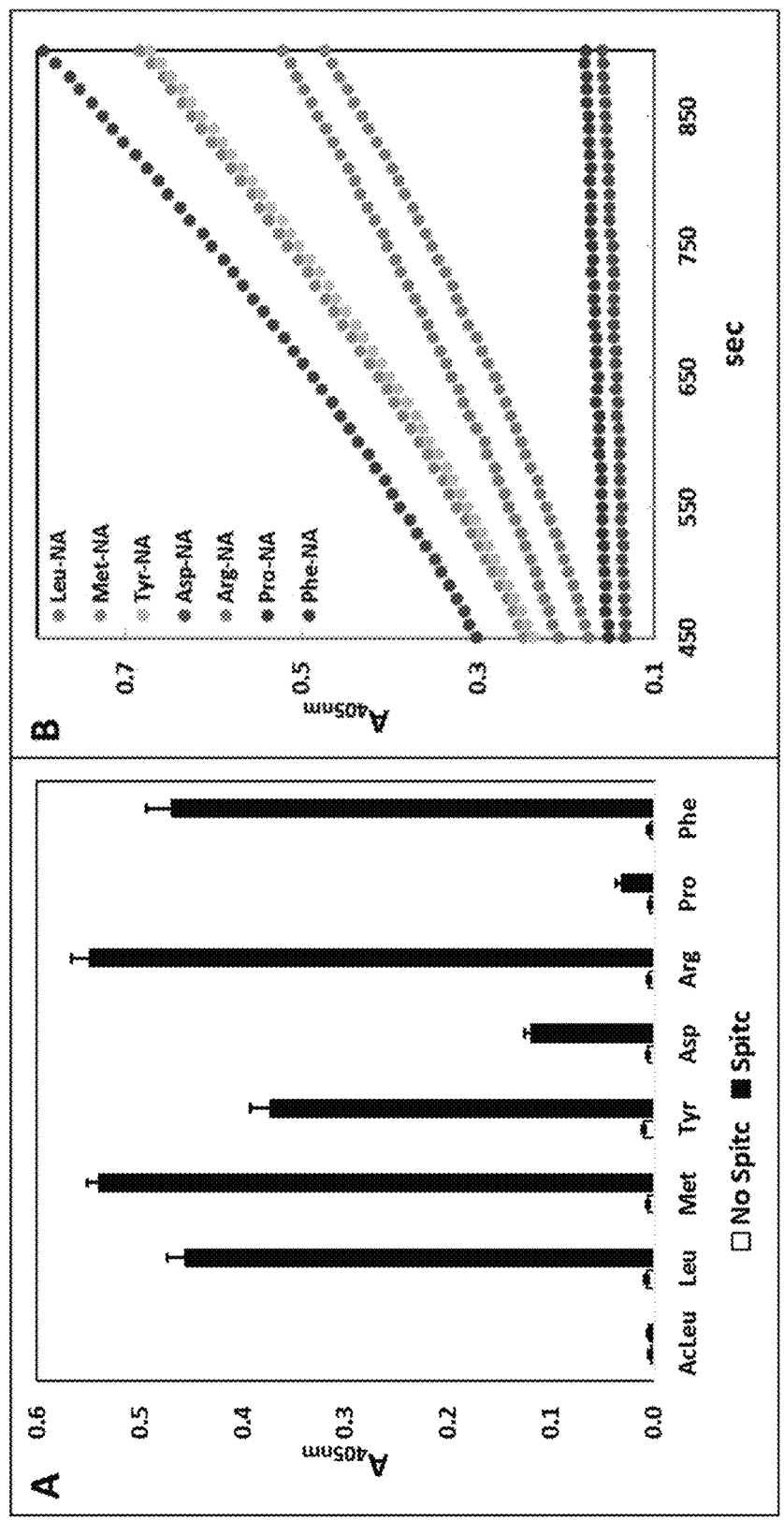
FIG. 16. Spontaneous Edman degradation of different amino acid p-nitroanilide substrates. A. Sulfophenyl isothiocyanate (SPITC, 15 mM) and substrate (1.5 mM) were incubated for 30 min at 40° C. in 300 mM triethanolamine in 50% ACN, after which the released p-nitroanilide was quantified by measuring the absorbance at 405 nm. B. Time-kinetic measurement of SPITC-induced amino acid p-nitroanilide substrate cleavage.

To check the spontaneous cleavage activity of the Edman reagent 4-sulfophenyl isothiocyanate (SPITC) on different amino acid p-nitroanilide substrates, 5 µl of 24 mM amino acid p-nitroanilide substrate (in methanol) and 240 mM SPITC (in water) was added to 70 µl 300 mM triethanolamine (in 50% acetonitrile (pH 9), and incubated for 30 min at 40° C. An endpoint activity measurement divides the tested amino acid substrates into fast-cleaved substrates (L, M, Y, R, F) and slow-cleaved substrates (D, P) (FIG. 16A). A time-kinetic assay shows the differences in reaction kinetics of the same set of substrates (FIG. 16B). Importantly, this spontaneous cleavage activity is also observed under conditions that are not typically used during the cleavage step in the classic Edman degradation reaction. In classic Edman degradation, ITC coupling is achieved under mild alkaline conditions (pyridine, trimethylamine, N-methylpiperidine) and amino acid cleavage under acidic conditions (trifluoroacetic acid). Here both ITC coupling and amino acid cleavage is achieved under mild alkaline conditions (triethanolamine).

Experimental Procedures
Transformation of *E. coli*

Defrost chemocompetent *E. coli* BL21(DE3) cells on ICE (NEB), add 100 ng plasmid DNA and keep on ice for 30 min. Incubate in warm water bath at 42° C. for 1.5 min and put on ice for 10 min. Add 1 ml LB medium to the vial and let it rest (LAF) with tape on shaker for 1 h at 37° C. Plate on LB-Kan agar plates (50 μg/ml kanamycin) and grow overnight at 37° C.

Culture Picking

Pick colonies from the plate (store plate at 4° C.) and add the colonies to 10 ml liquid TB medium+50 μg/ml Kan. Grown overnight at 37° C., prepare 500 μl aliquots (+500 μl glycerol) and store at −80° C.

Cloning

Figure 9:
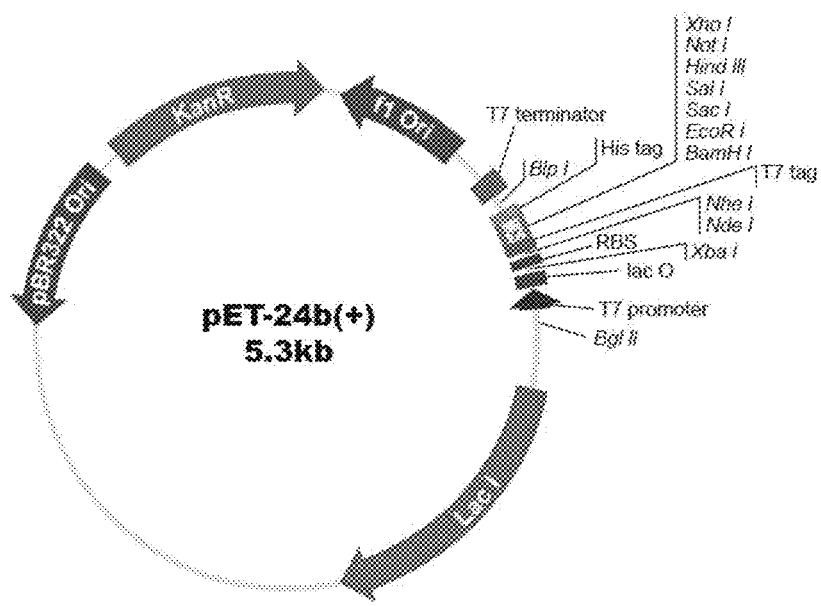
FIG. 9. Molecular map of the pET24b(+) plasmid.

For cloning, the pET-24b(+) plasmid was used (FIG. 9).

Ni-NTA Purification

Load 200 μl of lysate (in PBS+10 mM imidazole) onto a pre-equilibrated Qjagen Ni-NTA spin column and centrifuge at 100×g for 5 min. Wash the spin column 3× with 500 μl PBS+20 mM imidazole and elute with 500 μl PBS+250 mM imidazole.

Heat Treatment

Heat sample at 80° C. for 30 min and centrifuge at full speed for 10 min.

The invention claimed is:

1. A method of determining an identity of an N-terminal amino acid of a polypeptide, the method comprising:

contacting the polypeptide with one or more terminal amino acid binding proteins and a cleavage-inducing agent;

measuring residence times of the one or more terminal amino acid binding proteins on the N-terminal amino acid, wherein each residence time corresponds to a binding event between a terminal amino acid binding protein and the N-terminal amino acid; and determining the identity of the N-terminal amino acid by comparing the measured residence times to a set of reference residence time values characteristic for the one or more terminal amino acid binding proteins and a set of N-terminal amino acids.

2. The method of claim 1, wherein the residence times correspond to cycles of association/dissociation between the one or more terminal amino acid binding proteins and the N-terminal amino acid.

3. The method of claim 2, wherein the residence times correspond to at least 3 cycles of association/dissociation.

4. The method of claim 2, wherein the residence times correspond to at least 10 cycles of association/dissociation.

5. The method of claim 2, wherein the residence times correspond to at least 20 cycles of association/dissociation.

6. The method of claim 1, wherein at least one of the one or more terminal amino acid binding proteins comprises an optical, electrical, or plasmonic label.

7. The method of claim 1, wherein the residence times are measured optically, electrically, or plasmonically.

8. The method of claim 1, wherein at least one of the one or more terminal amino acid binding proteins is a catalytically inactive aminopeptidase.

9. The method of claim 1, wherein the cleavage-inducing agent is a catalytically active aminopeptidase.

10. The method of claim 1, wherein the polypeptide is immobilized on a surface.

11. The method of claim 10, wherein the polypeptide is immobilized on the surface via its C-terminus or via a peptide moiety C-terminal to a first peptide bond of the polypeptide.

12. The method of claim 1, further comprising, after the measuring:
   allowing the cleavage-inducing agent to cleave the N-terminal amino acid from the polypeptide.

13. The method of claim 12, wherein the cleavage-inducing agent is a thermophilic and/or solvent resistant aminopeptidase, and the polypeptide is subjected to conditions to allow the cleavage-inducing agent to cleave the N-terminal amino acid from the polypeptide.

14. The method of claim 12, wherein the one or more terminal amino acid binding proteins bind the N-terminal amino acid at a faster rate than a time required for the cleavage-inducing agent to cleave the N-terminal amino acid from the polypeptide.

* * * * *

SEQUENCE LISTING

```
Sequence total quantity: 10
SEQ ID NO: 1            moltype = AA  length = 346
FEATURE                 Location/Qualifiers
source                  1..346
                        mol_type = protein
                        organism = Trypanosoma cruzi
SEQUENCE: 1
MAPAAVDWRA RGAVTAVKDQ GQCGSCWAFS AIGNVECQWF LAGHPLTNLS EQMLVSCDKT  60
DSGCSGGLMN NAFEWIVQEN NGAVYTEDSY PYASGEGISP PCTTSGHTVG ATITGHVELP  120
QDEAQIAAWL AVNGPVAVAV DASSWMTYTG GVMTSCVSEQ LDHGVLLVGY NDSAAVPYWI  180
IKNSWTTQWG EEGYIRIAKG SNQCLVKEEA SSAVVGGPGP TPEPTTTTTT SAPGPSPSYF  240
VQMSCTDAAC IVGCENVTLP TGQCLLTTSG VSAIVTCGAE TLTEEVFLTS THCSGPSVRS  300
SVPLNKCNRL LRGSVEFFCG SSSSGRLADV DRQRRHQPYH SRHRRL                346

SEQ ID NO: 2            moltype = AA  length = 216
FEATURE                 Location/Qualifiers
source                  1..216
                        mol_type = protein
                        organism = Trypanosoma cruzi
SEQUENCE: 2
MAPAAVDWRA RGAVTAVKDQ GQCGSCWAFS AIGNVECQWF LAGHPLTNLS EQMLVSCDKT  60
DSGCSGGLMN NAFEWIVQEN NGAVYTEDSY PYASGEGISP PCTTSGHTVG ATITGHVELP  120
QDEAQIAAWL AVNGPVAVAV DASSWMTYTG GVMTSCVSEQ LDHGVLLVGY NDSAAVPYWI  180
IKNSWTTQWG EEGYIRIAKG SNQCLVKEEA SSAVVG                           216

SEQ ID NO: 3            moltype = AA  length = 346
FEATURE                 Location/Qualifiers
REGION                  1..346
                        note = engineered cruzipain T. cruzi without labels
source                  1..346
                        mol_type = protein
                        organism = synthetic construct
SEQUENCE: 3
MAPAAVDWRA RGAVTAVKDQ GQCGSGWAFS AIGNVECQWF LAGHPLTNLS EQMLVSCDKT  60
DSGCSSGLMN NAFEWIVQEN NGAVYTEDSY PYASGEGISP PCTTSGHTVG ATITGHVELP  120
QDEAQIAAWL AVNGPVAVCV DASSWMTYTG GVMTSCVSEQ LDHGVLLVGY NDSAAVPYWI  180
IKNSWTTQWG EEGYIRIAKG SNQCLVKEHA SSAVVGGPGP TPEPTTTTTT SAPGPSPSYF  240
VQMSCTDAAC IVGCENVTLP TGQCLLTTSG VSAIVTCGAE TLTEEVFLTS THCSGPSVRS  300
SVPLNKCNRL LRGSVEFFCG SSSSGRLADV DRQRRHQPYH SRHRRL                346

SEQ ID NO: 4            moltype = AA  length = 216
FEATURE                 Location/Qualifiers
REGION                  1..216
                        note = engineered cruzain T. cruzi without labels
source                  1..216
                        mol_type = protein
                        organism = synthetic construct
SEQUENCE: 4
MAPAAVDWRA RGAVTAVKDQ GQCGSGWAFS AIGNVECQWF LAGHPLTNLS EQMLVSCDKT  60
DSGCSSGLMN NAFEWIVQEN NGAVYTEDSY PYASGEGISP PCTTSGHTVG ATITGHVELP  120
QDEAQIAAWL AVNGPVAVCV DASSWMTYTG GVMTSCVSEQ LDHGVLLVGY NDSAAVPYWI  180
IKNSWTTQWG EEGYIRIAKG SNQCLVKEHA SSAVVG                           216

SEQ ID NO: 5            moltype = AA  length = 353
FEATURE                 Location/Qualifiers
REGION                  1..353
                        note = engineered cruzipain T. cruzi with labels
source                  1..353
                        mol_type = protein
                        organism = synthetic construct
SEQUENCE: 5
MCAPAAVDWR ARGAVTAVKD QGQCGSGWAF SAIGNVECQW FLAGHPLTNL SEQMLVSCDK  60
```

-continued

```
TDSGCSSGLM NNAFEWIVQE NNGAVYTEDS YPYASGEGIS PPCTTSGHTV GATITGHVEL  120
PQDEAQIAAW LAVNGPVAVC VDASSWMTYT GGVMTSCVSE QLDHGVLLVG YNDSAAVPYW  180
IIKNSWTTQW GEEGYIRIAK GSNQCLVKEH ASSAVVGGPG PTPEPTTTTT TSAPGPSPSY  240
FVQMSCTDAA CIVGCENVTL PTGQCLLTTS GVSAIVTCGA ETLTEEVFLT STHCSGPSVR  300
SSVPLNKCNR LLRGSVEFFC GSSSSGRLAD VDRQRRHQPY HSRHRRLHHH HHH         353

SEQ ID NO: 6           moltype = AA  length = 223
FEATURE                Location/Qualifiers
REGION                 1..223
                       note = engineered cruzipain T. cruzi with labels
source                 1..223
                       mol_type = protein
                       organism = synthetic construct
SEQUENCE: 6
MCAPAAVDWR ARGAVTAVKD QGQCGSGWAF SAIGNVECQW FLAGHPLTNL SEQMLVSCDK  60
TDSGCSSGLM NNAFEWIVQE NNGAVYTEDS YPYASGEGIS PPCTTSGHTV GATITGHVEL  120
PQDEAQIAAW LAVNGPVAVC VDASSWMTYT GGVMTSCVSE QLDHGVLLVG YNDSAAVPYW  180
IIKNSWTTQW GEEGYIRIAK GSNQCLVKEH ASSAVVGHHH HHH                    223

SEQ ID NO: 7           moltype = AA  length = 408
FEATURE                Location/Qualifiers
source                 1..408
                       mol_type = protein
                       organism = Thermus aquaticus
SEQUENCE: 7
MDAFTENLNK LAELAIRVGL NLEEGQEIVA TAPIEAVDFV RLLAEKAYEN GASLFTVLYG  60
DNLIARKRLA LVPEAHLDRA PAWLYEGMAK AFHEGAARLA VSGNDPKALE GLPPERVGRA  120
QQAQSRAYRP TLSAITEFVT NWTIVPFAHP GWAKAVFPGL PEEEAVQRLW QAIFQATRVD  180
QEDPVAAWEA HNRVLHAKVA FLNEKRFHAL HFQGPGTDLT VGLAEGHLWQ GGATPTKKGR  240
LCNPNLPTEE VFTAPHRERV EGVVRASRPL ALSGQLVEGL WARFEGGVAV EVGAEKGEEV  300
LKKLLDTDEG ARRLGEVALV PADNPIAKTG LVFFDTLFDE NAASHIAFGQ AYAENLEGRP  360
SGEEFRRRGG NESMVHVDWM IGSEEVDVDG LLEDGTRVPL MRRGRWVI                408

SEQ ID NO: 8           moltype = AA  length = 415
FEATURE                Location/Qualifiers
REGION                 1..415
                       note = labeled TaqAPT
source                 1..415
                       mol_type = protein
                       organism = synthetic construct
SEQUENCE: 8
MCDAFTENLN KLAELAIRVG LNLEEGQEIV ATAPIEAVDF VRLLAEKAYE NGASLFTVLY  60
GDNLIARKRL ALVPEAHLDR APAWLYEGMA KAFHEGAARL AVSGNDPKAL EGLPPERVGR  120
AQQAQSRAYR PTLSAITEFV TNWTIVPFAH PGWAKAVFPG LPEEEAVQRL WQAIFQATRV  180
DQEDPVAAWE AHNRVLHAKV AFLNEKRFHA LHFQGPGTDL TVGLAEGHLW QGGATPTKKG  240
RLCNPNLPTE EVFTAPHRER VEGVVRASRP LALSGQLVEG LWARFEGGVA VEVGAEKGEE  300
VLKKLLDTDE GARRLGEVAL VPADNPIAKT GLVFFDTLFD ENAASHIAFG QAYAENLEGR  360
PSGEEFRRRG GNESMVHVDW MIGSEEVDVD GLLEDGTRVP LMRRGRWVIH HHHHH       415

SEQ ID NO: 9           moltype = AA  length = 12
FEATURE                Location/Qualifiers
REGION                 1..12
                       note = test peptide
source                 1..12
                       mol_type = protein
                       organism = synthetic construct
SEQUENCE: 9
NNGGNNGGRG NK                                                      12

SEQ ID NO: 10          moltype = AA  length = 11
FEATURE                Location/Qualifiers
REGION                 1..11
                       note = peptide substrates
source                 1..11
                       mol_type = protein
                       organism = synthetic construct
SEQUENCE: 10
DGGNNGGKGG K                                                       11
```